(12) United States Patent
Beliën

(10) Patent No.: US 12,090,124 B2
(45) Date of Patent: Sep. 17, 2024

(54) PHARMACEUTICAL COMBINATION FOR USE IN AGE- RELATED AND/OR DEGENERATIVE DISEASES

(71) Applicant: REJUVENATE BIOMED, Heusden-Zolder (BE)

(72) Inventor: Ann Beliën, Heusden-Zolder (BE)

(73) Assignee: REJUVENATE BIOMED NV, Heusden-Zolder (BE)

( * ) Notice: Subject to any disclaimer, the term of this patent is extended or adjusted under 35 U.S.C. 154(b) by 29 days.

(21) Appl. No.: 17/255,662

(22) PCT Filed: Jul. 1, 2019

(86) PCT No.: PCT/EP2019/067645
§ 371 (c)(1),
(2) Date: Dec. 23, 2020

(87) PCT Pub. No.: WO2020/002715
PCT Pub. Date: Jan. 2, 2020

(65) Prior Publication Data
US 2021/0267918 A1   Sep. 2, 2021

(51) Int. Cl.
| | |
|---|---|
| *A61K 31/155* | (2006.01) |
| *A61K 31/13* | (2006.01) |
| *A61K 31/27* | (2006.01) |
| *A61K 31/445* | (2006.01) |
| *A61K 31/55* | (2006.01) |
| *A61P 21/06* | (2006.01) |
| *A61P 25/28* | (2006.01) |
| *A61P 39/00* | (2006.01) |

(52) U.S. Cl.
CPC ............ *A61K 31/155* (2013.01); *A61K 31/13* (2013.01); *A61K 31/27* (2013.01); *A61K 31/445* (2013.01); *A61K 31/55* (2013.01); *A61P 21/06* (2018.01); *A61P 25/28* (2018.01); *A61P 39/00* (2018.01)

(58) Field of Classification Search
CPC .................................................... A61K 31/155
See application file for complete search history.

(56) References Cited

FOREIGN PATENT DOCUMENTS

| CN | 103860532 A | 6/2014 | |
|---|---|---|---|
| CN | 104623671 B | 11/2017 | |
| WO | WO-0041540 A2 * | 7/2000 | ............ A23L 33/105 |
| WO | WO-2009039313 A1 * | 3/2009 | ......... A61K 2300/00 |
| WO | WO-2012012156 A1 * | 1/2012 | ............ A61K 31/155 |

OTHER PUBLICATIONS

Suzanne M. de la Monte, "Insulin resistance and Alzheimer's Disease", BMB rep. Aug. 31, 2009, pp. 1-13 (Year: 2009).*
Burns et al., "Lean Mass is Reduced in Early Alzheimer's Disease and Associated with Brain Atrophy", Arch Neurol. Apr. 1, 2011, pp. 1-13 (Year: 2011).*
Almed et al., "Effect of Metformin on Adult Hippocampal Neurogenesis: Comparison with Donepezil and Links to Cognition", J Mol Neurosci, Apr. 4, 2017, pp. 88-98 (Year: 2017).*
Huri et al., "Glycemic control and antidiabetic drugs in type 2 diabetes mellitus patients with renal complications", Drug Des Devel Ther, Aug. 7, 2015 (Year: 2015).*
Long et al., "Metformin to Augment Strength Training Effective Response in Seniors (MASTERS)", Trials. Apr. 26, 2017 (Year: 2017).*
Sramek JJ, Frackiewicz EJ, Cutler NR, "Review of the acetylcholinesterase inhibitor galanthamine", Expert Opin Investig Drugs. Oct. 2000 (Year: 2000).*
International Search Report mailed Sep. 25, 2019 in reference to co-pending European Patent Application No. PCT/EP2019/067645 filed Jul. 1, 2019.
De Haes, et al., "Metformin promotes lifespan through mitohormesis via the peroxiredoxin PRDX-2", PNAS CrossMark, pages E2501-E2509, Jun. 2, 2014.
Wilkinson, et al., "The age-related loss of skeletal muscle mass and function: Measurement and physiology of muscle fibre atrophy and muscle fibre loss in humans", Ageing Research Reviews, vol. 47, pp. 123-132, 2018.
Lucanic, et al., "Standardized Protocols from the Caenorhabditis Intervention Testing Program 2013-2016: Conditions and Assays used for Quantifying the Development, Fertility and Lifespan of Hermaphroditic Caenorhabditis Strains", Proto. Exch., pp. 1-30, 2017.
Keith, et al., "The C. elegans healthspan and stress-resistance assay toolkit", Methods, vol. 68, pp. 476-486, 2014.
Hahm, et al., "C. elegans maximum velocity correlates with healthspan and is maintained in worms with an insulin receptor mutation", Nature Communications, pp. 1-7, 2015.
Hsu, et al., "Identification by machine vision of the rate of motor activity decline as a lifespan predictor in C. elegans", Neurobiology Aging, vol. 9, pp. 1498-1503, Sep. 30, 2009.
Peymen, et al., "Myoinhibitory peptide signaling modulates aversive gustatory learning in Caenorhabditis elegans", PLOS Genetics, pp. 1-21, Feb. 19, 2019.
Dues, et al., "Aging Causes Decreased Resistance to Multiple Stresses and a Failure to Activate Specific Stress Response Pathways", GFP Report, pp. 1-35, 2016.
Mcelwee, et al., "Evolutionary conservation of regulated longevity assurance mechanisms", Genome Biology, pp. 1-16, 2007.
Detienne, et al., "SKN-1-independent transcriptional activation of glutathione S-transferase 4 (GST-4) by EGF signaling", WORM, vol. 5, No. 4, pp. 1-11, 2016.

(Continued)

*Primary Examiner* — John S Kenyon
*Assistant Examiner* — Gillian A Hutter
(74) *Attorney, Agent, or Firm* — Dinsmore & Shohl LLP

(57) ABSTRACT

The present invention relates to a pharmaceutical combination for use in the treatment, prevention and/or stabilization of age-related diseases and/or degenerative diseases. In particular, said pharmaceutical combination comprises a biguanide and an acetylcholinesterase inhibitor and/or an N-oxide, a hydrate, a pharmaceutically acceptable salt or solvate thereof. The invention is further also directed to the use of said pharmaceutical combination for prevention, stabilization and/or reduction of age-related complaints and/or degenerative complaints; and for improving a measure of life span and/or health span.

10 Claims, 12 Drawing Sheets

(56) References Cited

OTHER PUBLICATIONS

Herndon, et al., "Stochastic and genetic factors influence tissue-specific decline in ageing C. elegans", Nature Publishing Group, vol. 419, pp. 808-814, Oct. 2002.

Borisy, et al., "Systematic discovery of multicomponent therapeutics", PNAS, vol. 100, No. 13, pp. 7977-7982, Jun. 24, 2003.

Cabreiro, et al., "Metformin Retards Aging in C. elegans by Altering Microbial Folate and Methionine Metabolism", CrossMark Cell, vol. 153, pp. 228-239, Mar. 28, 2013.

Blaauw, et al., "Akt activation prevents the force drop induced by eccentric contractions in dystrophin-deficient skeletal muscle", Human Molecular Genetics, vol. 17, No. 23, pp. 3686-3696, 2008.

Bendetto, et al., "LFASS: Label-Free Automated Survival Scoring for High-Throughput Nematode Assays", BioRxiv, pp. 1-23, Sep. 28, 2017.

Tezze, et al., "Age-Associated Loss of OPA1 in Muscle Impacts Muscle Mass, Metabolic Homeostasis, Systemic Inflammation, and Epithelial Senescence", Cell Metabolism Article, pages vol. 25, pp. 1374-1389, Jun. 6, 2017.

Cogliati, et al., "Mitochondrial Cristae Shape Determines Respiratory Chain Supercomplexes Assembly and Respiratory Efficiency", Cell, vol. 155, pp. 160-171, Sep. 26, 2013.

De V. Weir, "New methods for calculating metabolic rate with special reference to protein metabolism", The Journal of Physiology, vol. 109, p. 1, Aug. 1, 1949.

Mitchell, et al., "Effects of Sex, Strain, and Energy Intake on Hallmarks of Aging in Mice", Cell Metabolism, vol. 23, pp. 1093-1112, Jun. 14, 2016.

Liao, et al., "Fat Maintenance Is a Predictor of the Murine Lifespan Response to Dietary Restriction", Aging Cell, vol. 4, pp. 629-639, Aug. 2011.

Flegal, et al., "Association of All-Cause Mortality With Overwieght and Obesity Using Standard Body Mass Index Categories", JAMA, vol. 309, pp. 71-82, Jan. 2, 2013.

Kokkinos, "Physical Activity, Health Benefits, and Mortality Risk", International Scholarly Research Network, vol. 2012, pp. 1-14, 2012.

Churgin, et al., "Longitudinal imaging of Caenorhabditis elegans in a microfabricated device reveals variation in behavioral decline during aging", eLIFE, pp. 1-25, 2017.

\* cited by examiner

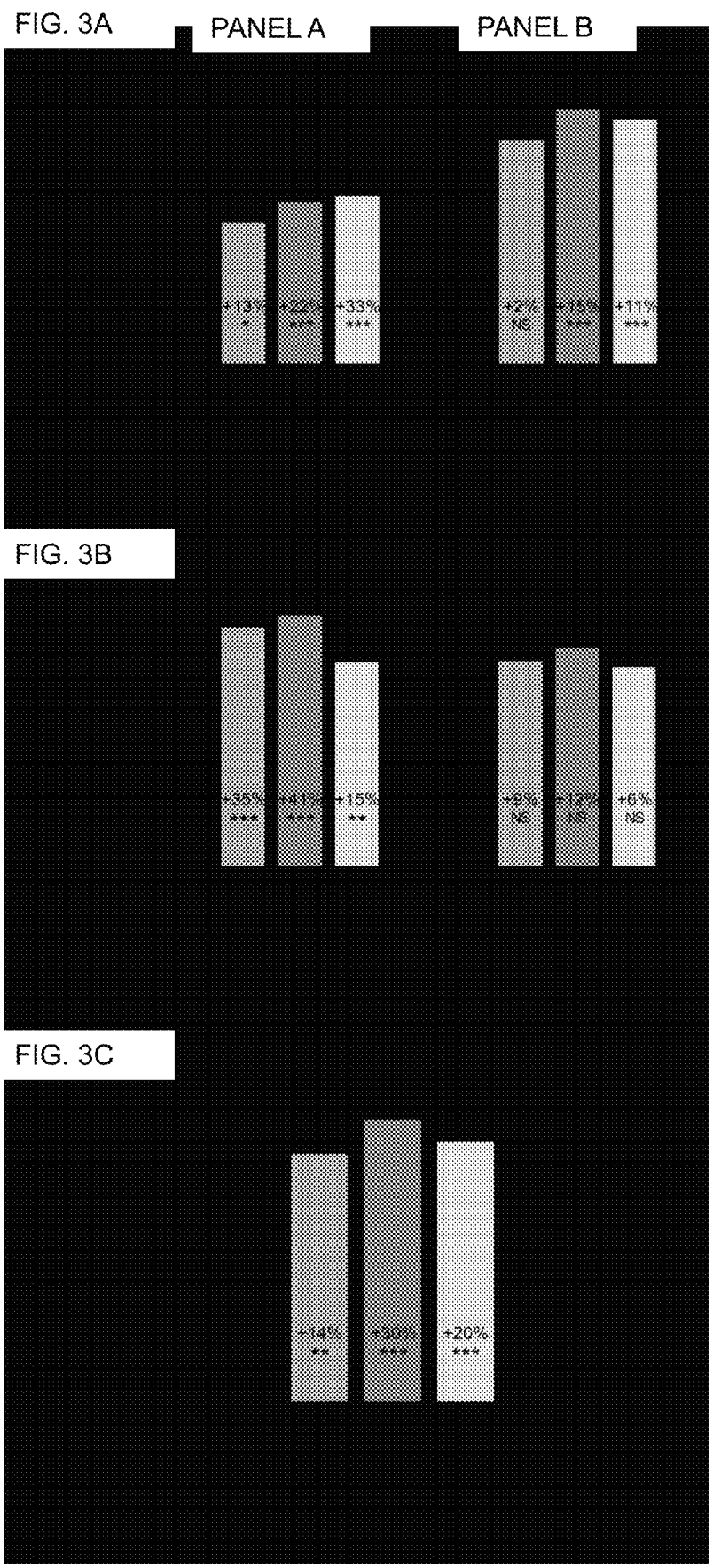

FIG. 6
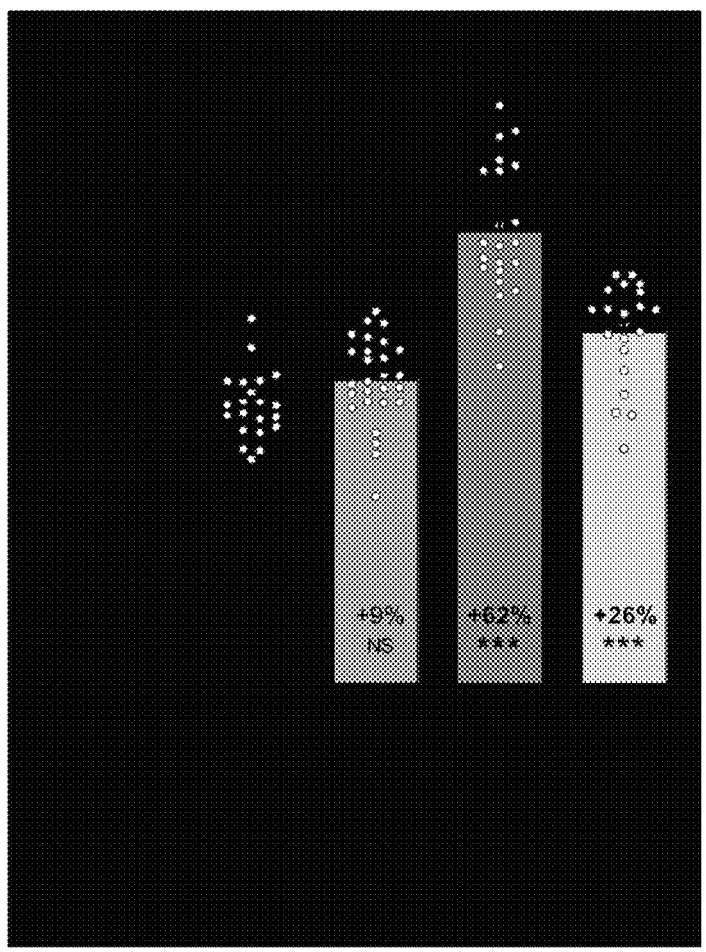
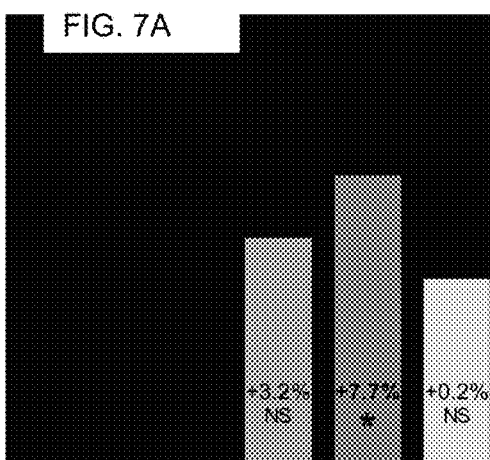
FIG. 7A
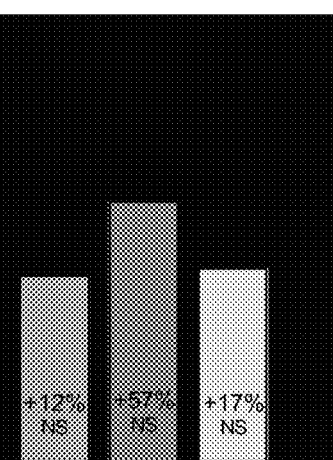
FIG. 7B

FIG. 8A
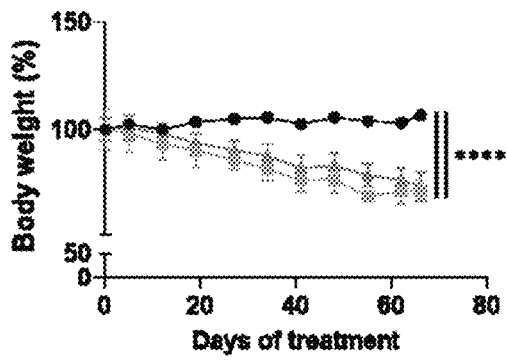
FIG. 8B
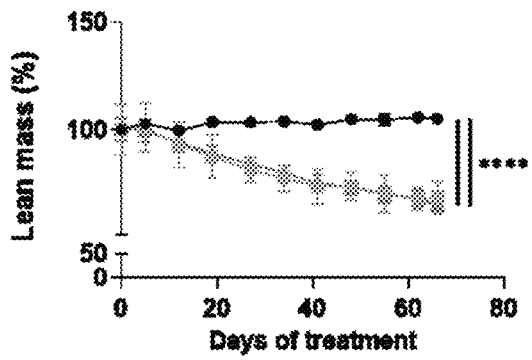
FIG. 8C
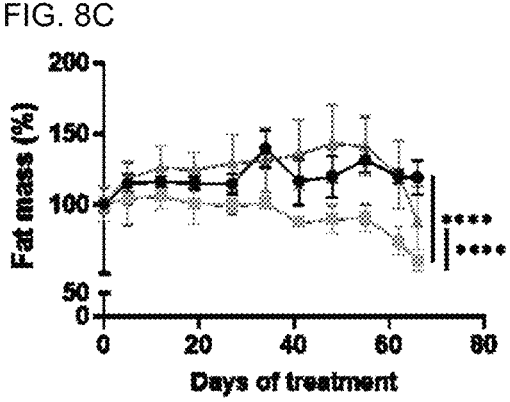
FIG. 8D
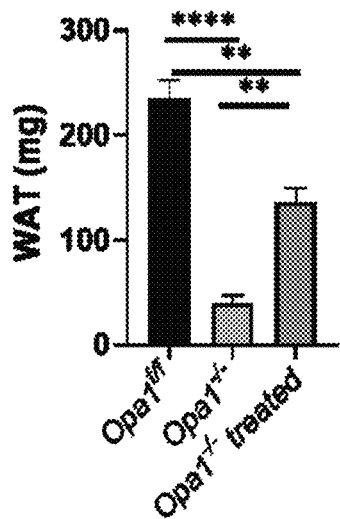
FIG. 8E
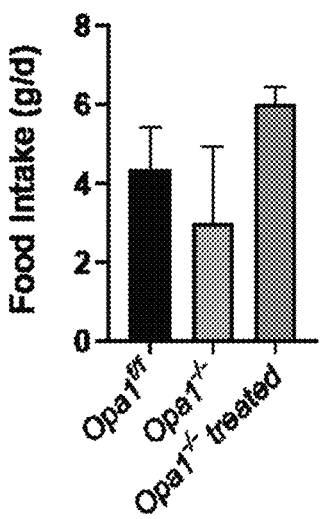

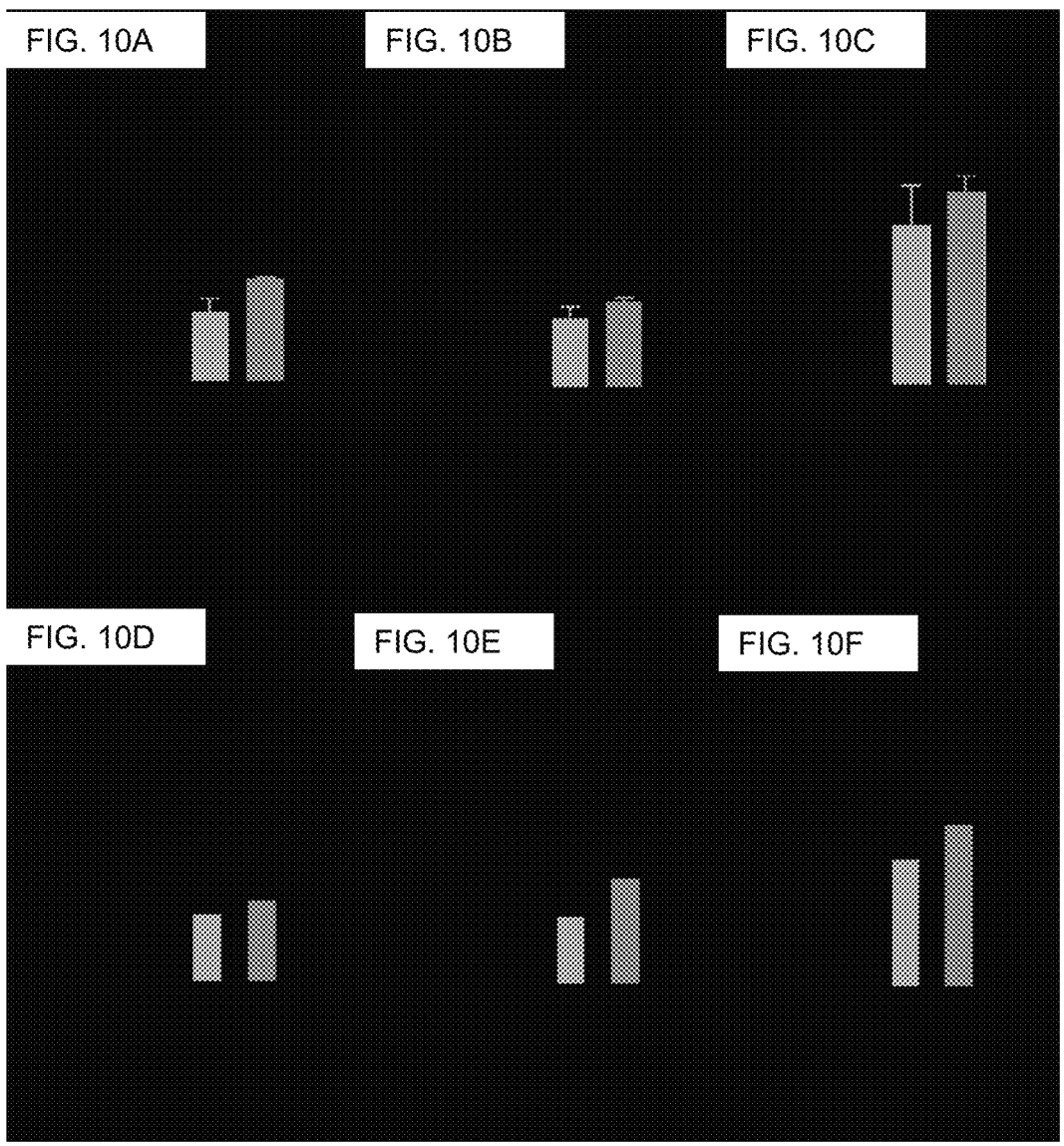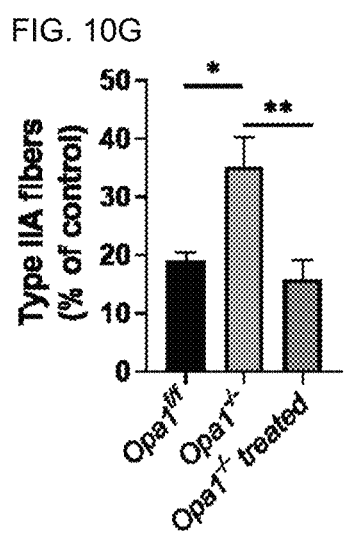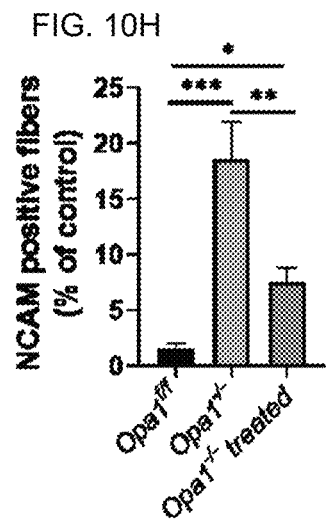

PHARMACEUTICAL COMBINATION FOR USE IN AGE- RELATED AND/OR DEGENERATIVE DISEASES

CROSS-REFERENCES TO RELATED APPLICATIONS

This application is a national-stage entry under 35 U.S.C. § 371 of International Application PCT/EP2019/067645, filed Jul. 1, 2019, which International Application claims the benefit of priority to European Patent Application No. 18180906.2, filed Jun. 29, 2018.

FIELD OF THE INVENTION

The present invention relates to a pharmaceutical combination for use in the treatment, prevention and/or stabilization of age-related diseases and/or degenerative diseases. In particular, said pharmaceutical combination comprises a biguanide and an acetylcholinesterase inhibitor and/or an N-oxide, a hydrate, a pharmaceutically acceptable salt or solvate thereof. The invention is also directed to the use of said pharmaceutical combination for prevention, stabilization and/or reduction of age-related complaints and/or degenerative complaints; and for improving a measure of life span and/or health span.

BACKGROUND TO THE INVENTION

Aging is the gradual loss of function and deterioration at the cellular, tissue, and organ level, leading to a progressive loss of physiological integrity, an increased susceptibility to disease and external stressors, and eventually leading to death. As the global population aging is increasing, the incidences of age-related diseases are expanding every year. And hence, numerous attempts have been made in trying to treat the age-related diseases, as well as trying to delay the onset of the complex process of aging. As a result, a number of age-related pathways have been identified that might be targeted to extend life span and health span. For example, there is overwhelming evidence that single gene mutations in nutrient-sensing pathways, such as insulin/insulin-like growth factor (IGF) signalling or the mechanistic target of rapamycin (mTOR) signalling pathways, extend life span and health span in invertebrates. These pathways have also been evaluated in mammalian models, in which health span and life span have been extended by genetic manipulation or drugs. Although this raises hope for new interventions, including drugs that slow the aging process and slow the appearance of age-related disease by modulating conserved pathways of aging, so far, except for some symptomatic treatment, unfortunately, there is no known intervention that was shown to efficiently slow down the human aging process. After all, in addition to treating existing diseases and disorders by means of medicine, the necessity and demand for measures for staying healthy and delaying aging is increasing.

Over the past decades, several model organisms have been used to gain more insight into the complex science of aging. Caenhorhabditis elegans (C. elegans) is a model animal organism commonly used for studying aging and age-related diseases, which has prominent advantages such as, short life cycle, simple experimental manipulation, and rich genetic resources. In addition, it is the first multicellular organism whose full genome sequencing has been completed, whose genome comprises ⅔ of human disease-related genes, and transgene diseases models can be easily obstructed by means of GFP labelling and whole-genome RNAi technology, it is possible to conduct a systematic and complete life-long follow-up research on degenerative pathology and potential drugs at the individual level, which is especially important to the study of aging and age-related diseases. Therefore, the use of C. elegans greatly promotes the explanation of age-related pathological mechanisms and the development of active compounds. Metformin has widely been used and is approved as an anti-diabetic drug for the treatment of type 2 diabetes. It increases insulin sensitivity, and thereby improves insulin action at the cellular level without affecting insulin secretion. It has also been shown that metformin exerts positive effects on several cardiovascular risk factors. Furthermore, it has been shown that metformin targets a number of aging mechanisms as well. Specifically for aging, metformin leads to decreased insulin levels, decreased IGF-1 signalling, inhibition of mTOR, inhibition of mitochondrial complex I in the electron transport chain and reduction of endogenous production of reactive oxygen species, activation of AMP-activated kinase (AMPK), and reduction in DNA damage. Metformin was also shown to favourably influence metabolic and cellular processes closely associated with the development of age-related conditions, such as inflammation, autophagy, and cellular senescence (Barzilai et al., Cell Metab. 2016). Using a C. elegans model system, the health-promoting and life-pronging effects of metformin in type 2 diabetes were confirmed as well.

Human studies have further shown that metformin significantly reduces the risk of cancer in diabetic patients (Fuming et al. Oncol Lett. 2018) and lowers the risk for coronary disease (Hong et al., Diabetes Care. 2014). However, all these effects have been observed when administering metformin at a considerably high therapeutic dose, which is at least 1500 mg/day or more. In addition, so far, no synergistic effects of metformin in combination with another compound on age-related diseases were identified.

Galantamine, an acetylcholinesterase inhibitor that allosterically modulates nicotinic receptors, is widely known as a drug administered to patients with Alzheimer's disease. In C. elegans, galantamine was shown to facilitate cholinergic neurotransmission in a similar manner as in humans, and to rescue the paralysis phenotype in a transgenic C. elegans Alzheimer's disease model (Xin et al., Plos One, 2013), but no effects on locomotion, mobility or other forms of age-related decline have been described for galantamine in C. elegans. In humans, it has been shown that galantamine significantly reduces death by myocardial infarction (Nordström et al., 2013). Furthermore, galantamine alleviates inflammation and insulin resistance in metabolic syndrome subjects (Consolim-Colombo et al.; JCI Insight. 2017). However, all these effects have been observed when administering galantamine in a considerably high therapeutic dose, which is at least 24 mg/day or more. Furthermore, also for galantamine, no synergistic effects on age-related diseases were identified when galantamine is combined with another compound.

In the present invention, the inventors have identified a potentiating and even a synergistic effect on age-related diseases using the biguanide metformin, in combination with the acetylcholinesterase inhibitor galantamine. In particular, this effect was even observed when administering at least one of the compounds, or both of the compounds, in their subtherapeutic dose.

SUMMARY OF THE INVENTION

The present invention provides a pharmaceutical combination comprising a biguanide, and/or an N-oxide, a hydrate, a pharmaceutically acceptable salt or solvate thereof, and an acetylcholinesterase inhibitor, and/or an N-oxide, a hydrate, a pharmaceutically acceptable salt or solvate thereof. Typical for the invention is that said pharmaceutical combination is for use in the treatment, prevention, stabilisation, delay in onset and/or reduction of symptoms of age-related and/or degenerative diseases. Further, the use of said pharmaceutical combination for prevention, stabilization, and/or reduction of age-related complaints and/or degenerative complaints and the use of said pharmaceutical combination for improving a measure of life span and/or health span is also disclosed.

The pharmaceutical combination according to all the different embodiments of the present invention comprises a biguanide and/or an N-oxide, a hydrate, a pharmaceutically acceptable salt or solvate thereof, and an acetylcholinesterase inhibitor and/or an N-oxide, a pharmaceutically acceptable salt or solvate thereof. In a further embodiment, the biguanide is metformin, also called 1,1-dimethyl-biguanide or N,N-dimethyl-biguanide. In another further embodiment of the present invention, the acetylcholinesterase inhibitor is selected from the group comprising galantamine, donepezil, rivastigmine and memantine. In yet a further embodiment, the pharmaceutical combination according to the invention comprises metformin in combination with galantamine, donepezil, rivastigmine and/or memantine, and/or an N-oxide, a hydrate, a pharmaceutically acceptable salt or solvate thereof. In an even further embodiment, the pharmaceutical combination according to the present invention comprises metformin and galantamine and/or an N-oxide, a hydrate, a pharmaceutically acceptable salt or solvate thereof. In still another embodiment, the pharmaceutical combination according to the present invention comprises metformin and donepezil, and/or an N-oxide, a hydrate, a pharmaceutically acceptable salt or solvate thereof, or metformin and memantine, and/or an N-oxide, a hydrate, a pharmaceutically acceptable salt or solvate thereof, or metformin and rivastigmine, and/or an N-oxide, a hydrate, a pharmaceutically acceptable salt or solvate thereof. In another embodiment the invention comprises metformin in combination with galantamine and donepezil and/or an N-oxide, a hydrate, a pharmaceutically acceptable salt or solvate thereof; or metformin in combination with galantamine and memantine and/or an N-oxide, a hydrate, a pharmaceutically acceptable salt or solvate thereof; or metformin in combination with galantamine and rivastigmine and/or an N-oxide, a hydrate, a pharmaceutically acceptable salt or solvate thereof; or metformin in combination with donepezil, rivastigmine and memantine and/or an N-oxide, a hydrate, a pharmaceutically acceptable salt or solvate thereof. In an even further embodiment the invention comprises metformin in combination with galantamine, donepezil and memantine and/or an N-oxide, a hydrate, a pharmaceutically acceptable salt or solvate thereof.

In a first objective of the present invention, the pharmaceutical combination in all its different embodiments as outlined herein above is for use in the treatment, prevention, stabilisation, delay in onset and/or reduction of the symptoms of age-related and/or degenerative diseases in a subject.

In a further embodiment, said age-related and/or degenerative diseases are selected from the group comprising immune diseases, inflammatory diseases, endocrine and metabolic diseases, diseases of the circulatory system, arthropathies, diseases of the digestive system, mitochondrial associated diseases, diseases of the neuro-musculoskeletal system, sarcopenia and frailty.

In a further and more preferred aspect, the age-related and/or degenerative diseases are selected from the group comprising age-related and/or degenerative diseases of the neuro-musculoskeletal system, frailty, inflammatory diseases and/or endocrine and metabolic disorders. In still another embodiment, the pharmaceutical combination according to all its embodiments is for use in the treatment, prevention, stabilisation, delay in onset and/or reduction of the symptoms of age-related and/or degenerative diseases selected from diseases of the neuro-musculoskeletal system and/or frailty. In the context of the present invention, age-related and/or degenerative diseases of the neuro-musculoskeletal system are selected from extrapyramidal and movement disorders, diseases of myoneural junction and muscle, systemic atrophies primarily affecting the central nervous system, muscular dystrophy, duchenne muscular dystrophy, spinal muscular atrophy and related diseases, motor neuron diseases such as amyotrophic lateral sclerosis, abnormal involuntary movements, abnormalities of gait and mobility, ataxia, mitochondrial associated neuro-musculoskeletal diseases and sarcopenia. Thus, in a specific aspect, the pharmaceutical combination according to all its embodiments is for use in the treatment, prevention, stabilisation, delay in onset and/or reduction of the symptoms of frailty.

In another specific aspect, the pharmaceutical combination according to all its embodiments is for use in the treatment, prevention, stabilisation, delay in onset and/or reduction of the symptoms of sarcopenia.

In yet another specific aspect, the pharmaceutical combination according to all its embodiments is for use in the treatment, prevention, stabilisation, delay in onset and/or reduction of extrapyramidal and movement disorders, diseases of myoneural junction and muscle, systemic atrophies primarily affecting the central nervous system, muscular dystrophy, duchenne muscular dystrophy, spinal muscular atrophy and related diseases, motor neuron diseases such as amyotrophic lateral sclerosis, abnormal involuntary movements, abnormalities of gait and mobility, or ataxia.

As already outlined above, and in a particular embodiment, the pharmaceutical combination according to all its embodiments is for use in the treatment, prevention, stabilisation, delay in onset and/or reduction of the symptoms of mitochondrial associated neuro-musculoskeletal diseases. Said mitochondrial associated neuro-musculoskeletal diseases are selected from central core disease and Optic Atrophy 1 (OPA1) associated diseases. Said OPA1 associated are selected from optic atrophy, OPA1 associated hypertension, and OPA1 associated atrophy.

In another aspect, the pharmaceutical combination according to all its different embodiments is for use in the treatment, prevention, stabilisation, delay in onset and/or reduction of symptoms of age-related and/or degenerative inflammatory diseases; in particular inflammatory diseases associated with increased cytokine levels.

In still another embodiment, the pharmaceutical combination according to all its different embodiments is for use in the treatment, prevention, stabilisation, delay in onset and/or reduction of symptoms of age-related and/or degenerative endocrine and metabolic disorders. In a further embodiment, said age-related and/or degenerative endocrine and metabolic disorders are selected from obesity, hypertension, metabolic syndrome; in particular sarcopenic obesity.

In another aspect, the pharmaceutical combination according to this invention is for use in the treatment, prevention, stabilisation, delay in onset and/or reduction of age-related immune diseases, such as age-related reduced immune response (e.g. response to vaccination) or dysfunction, bacterial infectious diseases and viral infectious diseases.

In another aspect, the pharmaceutical combination according to this invention is for use in the treatment, prevention, stabilisation, delay in onset and/or reduction of age-related endocrine and metabolic diseases, such as obesity, sarcopenic obesity, metabolic syndrome, type II diabetes and progeria.

In a further aspect, the pharmaceutical combination according to this invention is for use in the treatment, prevention, stabilisation, delay in onset and/or reduction of age-related diseases of the circulatory system, such as atherosclerosis, ischaemic heart disease, peripheral artery disease, or stroke.

In still another embodiment, the pharmaceutical combination according to this invention is for use in the treatment, prevention, stabilisation, delay in onset and/or reduction of age-related arthropathies, such as rheumatoid arthritis or osteoarthritis.

In another embodiment, the pharmaceutical combination of this present invention is for use in the treatment, prevention, stabilisation, delay in onset and/or reduction of age-related diseases of the digestive system, such as inflammatory liver disease, digestive tract disorders, or constipation.

As outlined above, typical for the invention is that said pharmaceutical combination is for use in the treatment, prevention, stabilisation, delay in onset and/or reduction of symptoms of age-related and/or degenerative diseases according to all the different embodiments. In a particular aspect of the invention, the pharmaceutical combination according to all its embodiments is for use in the prevention or delay in onset of said age-related and/or degenerative diseases. In another aspect, the pharmaceutical combination according to all its embodiments is for use in the treatment of age-related and/or degenerative diseases. In still a further aspect, the pharmaceutical combination according to all its embodiments is for use in the stabilisation of age-related and/or degenerative diseases according to all the different embodiments. In still another aspect, the pharmaceutical combination according to all its embodiments is for use in the reduction of symptoms of age-related and/or degenerative diseases according to all its embodiments. In a further aspect, said age-related and/or degenerative diseases are selected from age-related and/or degenerative diseases of the neuro-musculoskeletal system, sarcopenia and/or frailty.

In a second objective, the present invention provides the use of a pharmaceutical combination for prevention, stabilization and/or reduction of age-related complaints, degenerative dysfunctioning and/or degenerative complaints. In particular aspect, the present invention further provides the use of a pharmaceutical combination for prevention, stabilization and/or reduction of age-related complaints, degenerative dysfunctioning and/or degenerative complaints that are selected from the group comprising muscular weakness, decreased muscular strength, neuro-muscular degeneration, impaired mobility, and general weakness. In a further aspect, the invention provides the use of a pharmaceutical combination for prevention, stabilization and/or reduction of age-related complaints, degenerative dysfunctioning and/or degenerative complaints that are selected from the group comprising muscular weakness, decreased muscular strength, neuro-muscular degeneration, impaired mobility. In another particular aspect, and in view of the present invention, the age-related complaint is general weakness.

In a third objective, the present invention provides the use of a pharmaceutical combination for improving a measure of life span and/or health span. In a further aspect, the improved measure of life span and/or health span is selected from the group comprising an improvement in function in an age-related disability, a stabilisation of worsening of an age-related disability, the mitigation or stabilisation of age-related complaints, the mitigation or stabilisation of degenerative dysfunctioning and degenerative complaints, relative to the condition of the subject before administration of the pharmaceutical combination or relative to a control population.

The pharmaceutical combination of the uses of the different embodiments of the invention comprises a biguanide and/or an N-oxide, a hydrate, a pharmaceutically acceptable salt or solvate thereof, and an acetylcholinesterase inhibitor and/or an N-oxide, a pharmaceutically acceptable salt or solvate thereof. In a further embodiment, the biguanide is metformin, also called 1,1-dimethyl-biguanide or N, N-dimethyl-biguanide. In another further embodiment of the present invention, the acetylcholinesterase inhibitor is selected from the group comprising galantamine, donepezil, rivastigmine and memantine. In yet a further embodiment, the pharmaceutical combination according to the invention comprises metformin in combination with galantamine, donepezil, rivastigmine and/or memantine, and/or an N-oxide, a hydrate, a pharmaceutically acceptable salt or solvate thereof. In an even further embodiment, the pharmaceutical combination according to the present invention comprises metformin and galantamine and/or an N-oxide, a hydrate, a pharmaceutically acceptable salt or solvate thereof. In still another embodiment, the pharmaceutical combination according to the present invention comprises metformin and donepezil, and/or an N-oxide, a hydrate, a pharmaceutically acceptable salt or solvate thereof, or metformin and rivastigmine, and/or an N-oxide, a hydrate, a pharmaceutically acceptable salt or solvate thereof, or metformin and memantin, and/or an N-oxide, a hydrate, a pharmaceutically acceptable salt or solvate thereof.

In view of the present invention age-related complaints, degenerative dysfunctioning and/or degenerative complaints include but are not limited to muscular weakness, decreased muscular strength, neuro-muscular degeneration, impaired mobility, impaired immune response, metabolic imbalance, general weakness, and frailty. In a particular aspect, and in view of the present invention, age-related complaints, degenerative dysfunctioning and/or degenerative complaints are selected from muscular weakness, decreased muscular strength, neuro-muscular degeneration, impaired mobility. In another particular aspect, and in view of the present invention, the age-related complaint is general weakness.

In a further embodiment, the invention provides the use of a pharmaceutical combination as outlined above for the prevention, stabilization of worsening, delay in onset, and/or reduction of frailty, wherein the reduction in frailty or stabilization of worsening of frailty is selected from the group of parameters comprising increased strength, stabilisation of strength loss, increase in lean body mass, stabilisation of weight loss, improved mobility, stabilisation of mobility reduction, increased energy, stabilisation of energy loss, increased levels of activity, stabilisation of activity loss, increased endurance, stabilisation of endurance loss, enhanced behavioural response to a sensory cue, stabilisation of a behavioural response to a sensory cue, a decrease or stabilisation in one or more inflammatory markers or biomarkers, an improvement in glucose homeostasis and metabolic or katabolic state, an improvement in neurotransmission or neuromuscular transmission, and a decrease in one or more biomarkers of clotting activation, wherein the reduction or stabilisation is relative to the condition of the subject before administration of the pharmaceutical combination or relative to a control population.

In another further embodiment, the invention provides a pharmaceutical combination as outlined above for use in the treatment, prevention, stabilization of worsening, delay in onset, and/or reduction of frailty, wherein the reduction in frailty or stabilization of worsening of frailty is selected from the group of parameters comprising increased strength, stabilisation of strength loss, increase in lean body mass, stabilisation of weight loss, improved mobility, stabilisation of mobility reduction, increased energy, stabilisation of energy loss, increased levels of activity, stabilisation of activity loss, increased endurance, stabilisation of endurance loss, enhanced behavioural response to a sensory cue, stabilisation of a behavioural response to a sensory cue, a decrease or stabilisation in one or more inflammatory markers or biomarkers, an improvement in glucose homeostasis and metabolic or katabolic state, an improvement in neurotransmission or neuromuscular transmission, and a decrease in one or more biomarkers of clotting activation, wherein the reduction or stabilisation is relative to the condition of the subject before administration of the pharmaceutical combination or relative to a control population.

In another embodiment, the present invention provides the use of a pharmaceutical combination as outlined above for improving a measure of life span and/or health span, wherein the improved measure of life span and/or health span is selected from the group comprising an improvement in function in an age-related disability, a stabilisation of worsening of an age-related disability, the mitigation or stabilisation of age-related complaints, the mitigation or stabilisation of degenerative dysfunctioning and degenerative complaints, relative to the condition of the subject before administration of the pharmaceutical combination or relative to a control population. In another embodiment, the improved measure of life span and/or health span in the light of the present invention comprises an improvement in one or more parameters selected from the group consisting of cholesterol level, triglyceride level, high density lipoprotein level, low density lipoprotein level, leptin level, adiponectin level, inflammatory parameters, chronological versus biological age parameters and blood pressure, immunosenescence, wherein said measure of life span and/or health span is improved relative to the condition of the subject before administration of the pharmaceutical combination or relative to a control population.

In yet another embodiment, the present invention provides the use of a pharmaceutical combination as disclosed above for improving a measure of life span and/or health span, in particular for enhancing the ability to maintain homeostasis during the application of a stressor and/or a reduced time required to return to homeostasis after the application of a stressor.

In all different embodiments of the present invention, the pharmaceutical combination according to the invention can be administered in a therapeutic or subtherapeutic daily dose to a subject, in particular a human subject. In yet another embodiment, at least one of the components of the pharmaceutical combination of the present invention is administered in a subtherapeutic dose to a subject. In another embodiment, at least one of the components of the pharmaceutical combination according to this invention is administered in a therapeutic dose. In still another embodiment, one of the components of the pharmaceutical combination is administered in a subtherapeutic dose, whereas the other component is administered in a therapeutic dose. In another embodiment, all components of the pharmaceutical combination of the present invention are administered in a subtherapeutic dose to the subject.

In a preferred embodiment, in the pharmaceutical combination, the biguanide or its N-oxide, hydrate, pharmaceutically acceptable salt or solvate thereof is administered in a subtherapeutic dose, preferably in a subtherapeutic daily dose of maximum about 1500 mg/day per subject; more preferably in a subtherapeutic daily dose that is about 5 mg/day per subject or more and maximum about 1500 mg/day per subject; even more preferably in a subtherapeutic daily dose between about 5 mg/day and about 1000 mg/day per subject, even more preferably in a subtherapeutic daily dose between about 5 mg/day and about 850 mg/day per subject, or between about 5 mg/day and about 800 mg/day per subject, or between about 5 mg/day and about 750 mg/day per subject, or between about 5 mg/day and about 700 mg/day per subject, or between about 5 mg/day and about 500 mg/day per subject.

In another embodiment, in the pharmaceutical combination, the biguanide or its N-oxide, hydrate, pharmaceutically acceptable salt or solvate thereof can also be administered in a therapeutic dose, preferably in a therapeutic daily dose of more than 1500 mg/day per subject; even more preferably in a therapeutic daily dose that is more than 1500 mg/day and less than 3000 mg/day per subject.

In another preferred embodiment, in the pharmaceutical combination, the acetylcholinesterase inhibitor or its N-oxide, hydrate, pharmaceutically acceptable salt or solvate thereof is administered in a subtherapeutic dose, preferably in a subtherapeutic daily dose of less than about 16 mg/day per subject; even more preferably in a subtherapeutic dose that is more than about 0.08 mg/day and less than about 16 mg/day per subject, preferably less than about 12 mg/day per subject. In another embodiment, the acetylcholinesterase inhibitor or its N-oxide, hydrate, pharmaceutically acceptable salt or solvate thereof is administered in a subtherapeutic daily dose that is more than about 2 mg/day and less than about 16 mg/day per subject, preferably less than about 12 mg/day per subject.

In another embodiment, in the pharmaceutical combination, the acetylcholinesterase inhibitor or its N-oxide, hydrate, pharmaceutically acceptable salt or solvate thereof is administered in a therapeutic dose, preferably in a therapeutic daily dose of more than 16 mg/day per subject; even more preferably in a therapeutic daily dose that is between 16 mg/day and 24 mg/day per subject.

In another preferred embodiment, the pharmaceutical combination according to this invention is a pharmaceutical combination comprising a biguanide, preferably metformin and an acetylcholinesterase inhibitor, selected from galantamine, donepezil, rivastigmine or memantine, wherein both the biguanide and the acetylcholinesterase inhibitor are both administered in a subtherapeutic dose. In said context, the biguanide is administered in a subtherapeutic daily dose of maximum about 1500 mg/day per subject, preferably maximum about 1000 mg/day per subject; more preferably in a subtherapeutic daily dose that is about 5 mg/day or more and maximum about 1500 mg/day per subject; even more preferably in a subtherapeutic daily dose between about 5 and about 1000 mg/day per subject. Also in said context, the acetylcholinesterase inhibitor is administered in a subtherapeutic daily dose of less than about 16 mg/day per subject; even more preferably in a subtherapeutic dose that is more than about 0.08 mg/day and less than about 16 mg/day per subject, preferably less than about 12 mg/day per subject. In an even more preferred embodiment, in a subtherapeutic daily dose that is more than about 2 mg/day and less than about 16 mg/day per subject, preferably less than about 12 mg/day per subject. In an even more preferred embodiment, in a subtherapeutic daily dose that is between 3 mg/day and 12 mg/day per subject.

In another aspect of the invention, the pharmaceutical combination in all different embodiments of the invention is prepared for oral administration or any other non-invasive administration. The pharmaceutical combination according to the different embodiments of the invention is further characterized in that the biguanide and the acetylcholinesterase inhibitor or their N-oxide, hydrate, pharmaceutically acceptable salt or solvate are separately formulated into pharmaceutical compositions. In a further aspect, the biguanide and the acetylcholinesterase inhibitor or their N-oxide, hydrate, pharmaceutically acceptable salt or solvate are administered simultaneously to the subject. Alternatively, the biguanide and the acetylcholinesterase inhibitor or their N-oxide, hydrate, pharmaceutically acceptable salt or solvate are administered at different time points.

In another aspect, the biguanide and the acetylcholinesterase inhibitor or their N-oxide, hydrate, pharmaceutically acceptable salt or solvate are formulated in a single pharmaceutical formulation in the present pharmaceutical combination.

The present invention can be summarized in the following numbered embodiments:

1. A pharmaceutical combination for use in the treatment, prevention, stabilisation, delay in onset and/or reduction of the symptoms of age-related and/or degenerative diseases in a subject, said pharmaceutical combination comprising:
   a biguanide, and/or an N-oxide, a hydrate, a pharmaceutically acceptable salt or solvate thereof, and
   an acetylcholinesterase inhibitor, and/or an N-oxide, a hydrate, a pharmaceutically acceptable salt or solvate thereof.

2. The pharmaceutical combination for use according to embodiment 1 wherein the biguanide is metformin.

3. The pharmaceutical combination for use according to embodiment 1 wherein the acetylcholinesterase inhibitor is selected from the group comprising galantamine, donepezil, rivastigmine and memantine; preferably galantamine.

4. The pharmaceutical combination for use according to anyone of embodiments 1 to 3 wherein the age-related and/or degenerative diseases are selected from the group comprising immune diseases, endocrine and metabolic diseases, diseases of the circulatory system, arthropathies, diseases of the digestive system, diseases of the neuro-musculoskeletal system, inflammatory diseases, and frailty.

5. The pharmaceutical combination for use according to embodiment 4 wherein the immune diseases are selected from the group comprising age-related reduced immune response (e.g. response to vaccination), age-related immune dysfunction, bacterial infectious diseases and viral infectious diseases.

6. The pharmaceutical combination for use according to embodiment 4, wherein the endocrine and metabolic disorders are selected from the group comprising obesity, sarcopenic obesity, metabolic syndrome, type II diabetes, progeria; in particular sarcopenic obesity.

7. The pharmaceutical combination for use according to embodiment 4 wherein the diseases of the circulatory system are selected from the group comprising atherosclerosis, ischaemic heart disease, peripheral artery disease, and stroke.

8. The pharmaceutical combination for use according to embodiment 4 wherein the arthropathies are selected from the group comprising rheumatoid arthritis and osteoarthritis.

9. The pharmaceutical combination for use according to embodiment 4 wherein the diseases of the digestive system are selected from the group comprising gastritis, peptic ulcer disease, inflammatory liver disease, digestive tract disorders, and constipation.

10. The pharmaceutical combination for use according to embodiment 1 to 3, wherein the age-related and/or degenerative diseases are selected from age-related and/or degenerative diseases of the neuro-musculoskeletal system, frailty, inflammatory diseases, and/or endocrine and metabolic disorders.

11. The pharmaceutical combination for use according to embodiment 1 for use in the treatment, prevention, stabilisation, delay in onset and/or reduction of the symptoms of age-related and/or degenerative diseases of the neuro-musculoskeletal system and/or frailty.

12. The pharmaceutical combination for use according to embodiment 11, wherein the diseases of the neuro-musculoskeletal system are selected from the group comprising extrapyramidal and movement disorders, diseases of myoneural junction and muscle, systemic atrophies primarily affecting the central nervous system, muscular dystrophy, duchenne muscular dystrophy, spinal muscular atrophy and related diseases, motor neuron diseases such as amyotrophic lateral sclerosis, abnormal involuntary movements, abnormalities of gait and mobility, ataxia, mitochondrial associated neuromusculoskeletal diseases, and sarcopenia.

13. The pharmaceutical combination for use according to embodiment 11, wherein the diseases of the neuro-musculoskeletal system are selected from the group comprising extrapyramidal and movement disorders, diseases of myoneural junction and muscle, systemic atrophies primarily affecting the central nervous system, muscular dystrophy, duchenne muscular dystrophy, spinal muscular atrophy and related diseases, motor neuron diseases such as amyotrophic lateral sclerosis, abnormal involuntary movements, abnormalities of gait and mobility, or ataxia.

14. The pharmaceutical combination for use according to embodiment 11, wherein the disease of the neuro-musculoskeletal system is sarcopenia.

15. The pharmaceutical combination for use according to embodiment 11, wherein the disease of the neuro-musculoskeletal system 16. The pharmaceutical combination for use according to embodiment 1, wherein the age-related and/or degenerative diseases are mitochondrial associated neuro-musculoskeletal diseases; in particular mitochondrial associated neuromusculoskeletal diseases selected from central core disease and Optic Atrophy 1 (OPA1) associated diseases.

17. Use of a pharmaceutical combination for prevention, stabilization and/or reduction of age-related complaints and/or degenerative complaints, said pharmaceutical combination comprising:
   a biguanide, or an N-oxide, a hydrate, a pharmaceutically acceptable salt or solvate thereof, and
   an acetylcholinesterase inhibitor, or an N-oxide, a hydrate, a pharmaceutically acceptable salt or solvate thereof.

18. Use of a pharmaceutical combination for improving a measure of life span and/or health span, said pharmaceutical combination comprising:
   a biguanide, or an N-oxide, a hydrate, a pharmaceutically acceptable salt or solvate thereof, and an acetylcholinesterase inhibitor, an N-oxide, a hydrate, a pharmaceutically acceptable salt or solvate thereof.

19. The use of a pharmaceutical combination according to embodiment 18, wherein the improved measure of life span and/or health span is selected from the group comprising an improvement in function in an age-related disability, a stabilisation of worsening of an age-related disability, the mitigation or stabilisation of age-related complaints and/or degenerative complaints, relative to the condition of the subject before administration of the pharmaceutical combination or relative to a control population.

20. The use of a pharmaceutical combination according to embodiment 17 or 19, wherein age-related complaints and/or degenerative complaints are selected from the group comprising muscular weakness, decreased muscular strength, neuro-muscular degeneration, impaired mobility, reduced or impaired immune response, metabolic imbalance, general weakness, frailty.

21. The use of a pharmaceutical combination according to embodiment 17 or 19, wherein age-related complaints and/or degenerative complaints are selected from the group comprising muscular weakness, decreased muscular strength, neuro-muscular degeneration, and impaired mobility.

22. The use of a pharmaceutical combination according to embodiment 17 or 19, wherein the age-related complaint and/or degenerative complaint is general weakness.

23. The use of a pharmaceutical combination according to embodiment 20, wherein the reduction in frailty or stabilisation of worsening of frailty is selected from the group of parameters consisting of increased strength, stabilisation of strength loss, increase in lean body mass, stabilisation of weight loss, improved mobility, stabilisation of mobility reduction, increased energy, stabilisation of energy loss, increased levels of activity, stabilisation of activity loss, increased endurance, stabilisation of endurance loss, enhanced behavioural response to a sensory cue, stabilisation of a behavioural response to a sensory cue, a decrease or stabilisation in one or more inflammatory markers or biomarkers, an improvement in glucose homeostasis and metabolic or katabolic state, an improvement in neurotransmission or neuromuscular transmission, and a decrease in one or more biomarkers of clotting activation, wherein the reduction or stabilisation is relative to the condition of the subject before administration of the pharmaceutical combination or relative to a control population.

24. The use of a pharmaceutical combination according to embodiment 18, wherein the improved measure of life span and/or health span comprises an improvement in one or more parameters selected from the group consisting of cholesterol level, triglyceride level, high density lipoprotein level, low density lipoprotein level, leptin level, adiponectin level, inflammatory parameters, chronological versus biological age parameters and blood pressure, immunosenescence, wherein said measure of life span and/or health span is improved relative to the condition of the subject before administration of the pharmaceutical combination or relative to a control population.

25. The use of a pharmaceutical combination according to embodiment 18, wherein the improvement in a measure of life span and/or health span comprises an enhanced ability to maintain homeostasis during the application of a stressor and/or a reduced time required to return to homeostasis after the application of a stressor.

26. The use of a pharmaceutical combination according to anyone of embodiments 17 to 25, wherein the biguanide is metformin.

27. The use of a pharmaceutical combination according to anyone of embodiments 17 to 26 wherein the acetylcholinesterase inhibitor is selected from the group comprising galantamine, donepezil, rivastigmine and memantine.

28. The pharmaceutical combination for use according to anyone of embodiments 1 to 16, or the use of a pharmaceutical combination according to anyone of the embodiments 17 to 27, wherein the pharmaceutical combination is prepared for oral administration or any other non-invasive administration.

29. The pharmaceutical combination for use or the use of a pharmaceutical combination according to anyone of the preceding embodiments, wherein the biguanide and the acetylcholinesterase inhibitor or their N-oxide, hydrate, pharmaceutically acceptable salt or solvate are separately formulated into pharmaceutical compositions.

30. The pharmaceutical combination for use or the use of a pharmaceutical combination according to anyone of the preceding embodiments, wherein the biguanide and the acetylcholinesterase inhibitor or their N-oxide, hydrate, pharmaceutically acceptable salt or solvate are formulated in a single pharmaceutical formulation.

31. The pharmaceutical combination for use or the use of a pharmaceutical combination according to anyone of the preceding embodiments, wherein the biguanide and the acetylcholinesterase inhibitor or their N-oxide, hydrate, pharmaceutically acceptable salt or solvate are administered simultaneously.

32. The pharmaceutical combination for use or the use of a pharmaceutical combination according to anyone of the preceding embodiments, wherein biguanide and the acetylcholinesterase inhibitor or their N-oxide, hydrate, pharmaceutically acceptable salt or solvate are administered at different time points.

33. The pharmaceutical combination for use or the use of a pharmaceutical combination according to anyone of the preceding embodiments, wherein biguanide and the acetylcholinesterase inhibitor or their N-oxide, hydrate, pharmaceutically acceptable salt or solvate are administered in a subtherapeutic dose to the subject.

34. The pharmaceutical combination for use or the use of a pharmaceutical combination according to anyone of the preceding embodiments, wherein the subject is a human subject.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

FIG. 3A-FIG. 3C. Single dosing of *C. elegans* with galantamine and/or metformin positively impacts multiple locomotion parameters (i.e. mean activity (FIG. 3A) and maximal activity (FIG. 3B)) during aging, as well as the average number of 'healthy days' (FIG. 3C). The latter is a healthspan parameter, defined as the number of days of which the activity of an animal is higher than 15% of the mean maximal activity of the untreated control condition (within the same assay). In FIG. 3A, baseline activity (i.e. prior to a blue light stimulus) is shown in Panel A whereas stimulated activity (i.e. after a blue light stimulus) is shown in Panel B. Error bars indicate SEM. Statistical significance levels (and percentual changes) are indicated versus the untreated control at the bottom of each chart. Statistical significance versus '25 mM Met+100 UM Gal' is indicated via additional lines. $*p_{ANOVA}<0.05$, $p_{ANOVA}<0.01$, $*p_{ANOVA}<0.001$, NS not significant.

FIG. 6. Transcription of the cytoprotective glutathione S-transferase 4 (gst-4) gene is activated by Met and Gal in a synergetic fashion. Data from an in vivo gene transcription assay in *C. elegans* is shown. Each circle (biological replicate) consists of thousands of animals. Error bars indicate SEM. Pooled data from three independent assays is shown. Statistical significance levels (and percentual changes) are indicated versus the untreated control at the bottom. Statistical significance versus the '25 mM Met+100 UM Gal' is indicated via additional lines. $***p_{ANOVA}<0.001$, NS not significant.

FIG. 7A-FIG. 7B. Adult *C. elegans* treated with a combination of Met and Gal show an improved muscle morphology compared to untreated control animals. (FIG. 7A) Aspect ratio represents the measurement of myofilament length and width, whereas (FIG. 7B) smoothness represents a measure for perfect myofilament contour. Statistical significance levels (and percentual changes) are indicated versus the untreated control condition. $*p_{ANOVA}<0.05$, NS not significant.

FIG. 8A-FIG. 8I. Muscle specific Opa1$^{-/-}$ mice treated with combination of metformin and galantamine maintained fat mass, restored metabolism and prevented liver steatosis.

(FIG. 8A) Bodyweight, (FIG. 8B) lean mass and (FIG. 8C) fat mass measured in female Opa1$^{f/f}$ (control), Opa1$^{-/-}$ mice supplemented with and without metformin plus galantamine after tamoxifen treatment. (FIG. 8D) White adipose tissue (WAT) content of male Opa1$^{f/f}$, Opa1$^{-/-}$ mice supplemented with and without metformin plus galantamine. (FIG. 8E) Food consumption. (FIGS. 8F-FIG. 8H) In vivo metabolic response to the combination treatment. (FIG. 8F) depicting Oxygen consumption (VO$_2$) (FIG. 8G) Carbon dioxide production (VCO$_2$) (FIG. 8H) Energy expenditure (FIG. 8I) Skeletal muscle IL6 inflammatory levels. Data are mean±SEM, Females: n=2-4, Males: n=3, $*p<0.05$, $p<0.01$, $**p<0.0001$.

Specifically, (FIG. 9A) depicts time ran on treadmill performance and (FIG. 9B) grip strength measured in female Opa1$^{-/-}$ mice with and without metformin plus galantamine treatment 60 and 50 days after tamoxifen treatment respectively. (FIGS. 9C-FIG. 9F) Force-frequency curves performed in vivo on gastrocnemius muscles, with (FIG. 9C and FIG. 9D) depicting absolute force and (FIG. 9E and FIG. 9F) maximal specific force generated during tetanic contraction in respectively female and male Opa1$^{-/-}$ mice treated with and without metformin plus galantamine treatment. Data represent mean±SEM, Females: n=2-4, Males: n=3, $*p<0.05$, $**p<0.01$.

FIG. 10A-FIG. 10H. Combination of both metformin and galantamine partly preserved muscle mass in Opa1$^{-/-}$ mice.

(FIG. 10A-FIG. 10F) Muscle weights of female and male controls (Opa1$^{f/f}$), Opa1$^{-/-}$ mice supplemented with and without metformin plus galantamine treatment respectively, with (FIG. 10A and FIG. 10D) depicting Tibialis anterior (FIG. 10B and FIG. 10E) Gastrocnemius (FIG. 10C and FIG. 10F) Soleus (FIG. 10G) Quantification of myofiber number and of (FIG. 10H) denervated NCAM-positive fibers in female control (Opa1$^{f/f}$), Opa1$^{-/-}$ mice treated with and without metformin plus galantamine treatment. Data are mean±SEM, Females: n=2-4, Males: n=3, $*p<0.05$, $p<0.01$, $*p<0.001$ and $****p<0.0001$.

DETAILED DESCRIPTION OF THE INVENTION

Figure 1:
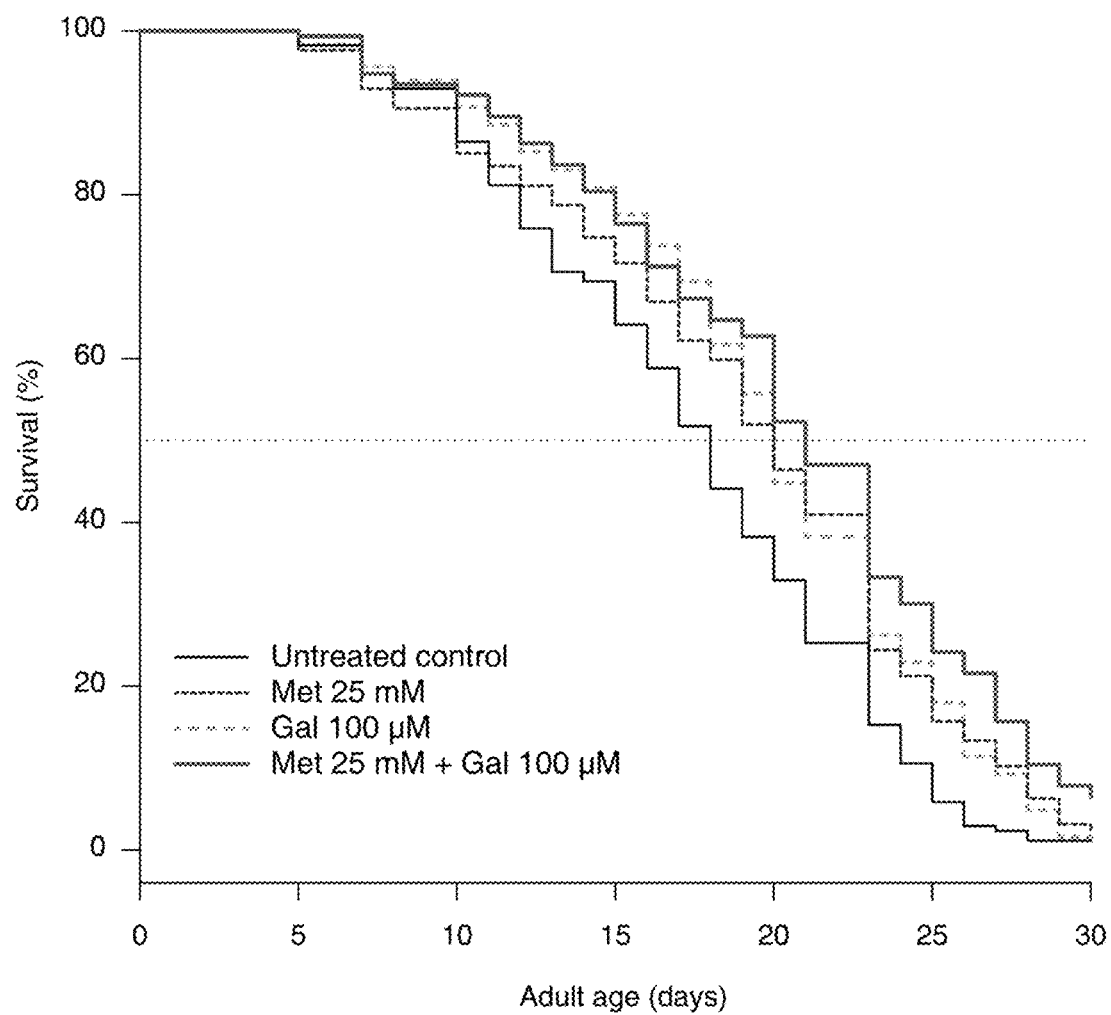
FIG. 1. Life span assay using *C. elegans* to evaluate the life-prolonging effect of a single dose of metformin, galantamine and the combination of metformin and galantamine. Pooled data from multiple assays, measuring *C. elegans* survival, is shown. Treatment started at the first day of adulthood and animals were dosed once. Full life span data are displayed in Table 1.

The present invention is directed to a pharmaceutical combination for use in the treatment, prevention, stabilization, delay in onset and/or reduction of the symptoms of age-related and/or degenerative diseases, in particular age-related and/or degenerative diseases of the neuro-musculo-skeletal system, sarcopenia and/or frailty.

In the light of the present invention, the term "treat" or "treatment" refers to an action resulting in a curative treatment or to a lessening or reduction in the severity of a symptom of or a disease or condition or to a lessening the frequency of outbreaks of a disease or disorder. The terms include a remitative treatment of a disorder (i.e. treatment that causes the disorder to enter remission). The term "treat" or "treatment" includes administration of an agent where the disease or condition is at least partially improved or ameliorated, and/or there is some alleviation, mitigation or decrease in at least one clinical symptom, and/or there is a delay in the progression of the condition or disease, and/or prevention or delay of the onset of the condition or disease.

Thus, the terms "treat" and "treatment" refer to both prophylactic and therapeutic treatment regimens. The term "treatment" is used interchangeably herein with the term "therapeutic method" and refers to both therapeutic and prophylactic/preventative measures. Those in need of treatment may include individuals already having a particular medical disorder as well as those who may ultimately acquire the disorder (i.e. those needing preventive measures).

As used herein, "prevention" or "prophylaxis" refers to methods in which the risk of developing a disease or a condition or symptom is reduced. Prevention includes the reduction in the risk of developing a disease or condition and/or a prevention of worsening of symptoms or progression of a disease or reduction in the risk of worsening of symptoms or progression of a disease or condition.

As used herein "stabilization" of the symptoms of age-related or degenerative diseases refers to the condition wherein there is neither a decrease nor an increase in the number and/or extent of severity of the symptoms.

As used herein "a combination" refers to any association between two or among more items. The association can be spatial or refer to the use of the two or more items for a common purpose. As used herein, a "composition", refers to any mixture of two or more products or compounds (e.g. agents, modulators, regulators, etc.). It can be a solution, a suspension, liquid, powder or a paste, aqueous or non-aqueous formulations or any combination thereof.

The present invention is thus directed to a pharmaceutical combination comprising a biguanide, and/or an N-oxide, a hydrate, a pharmaceutically acceptable salt or solvate thereof; and an acetylcholinesterase inhibitor, and/or an N-oxide, a hydrate, a pharmaceutically acceptable salt or solvate thereof.

The N-oxide forms are meant to comprise compounds wherein one or several nitrogen atoms are oxidized to the so-called N-oxide.

For pharmaceutical use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a pro-drug or pre-drug, such as an ester. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person; reference is for instance made to the salts, hydrates, solvates, etc. described in U.S. Pat. Nos. 6,372,778, 6,369,086, 6,369,087 and 6,372,733.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. In addition, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl-bromides and others. Other pharmaceutically acceptable salts include the sulfate salt ethanolate and sulfate salts.

Generally, for pharmaceutical use, the compounds of the inventions may be formulated as a pharmaceutical preparation or pharmaceutical composition comprising at least one compound of the invention and at least one pharmaceutically acceptable carrier, diluent or excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is again made to for instance U.S. Pat. Nos. 6,372,778, 6,369,086, 6,369,087 and 6,372,733, as well as to the standard handbooks, such as the latest edition of Remington's Pharmaceutical Sciences.

In the light of the present invention, an "age-related disease" refers to an abnormal condition characterized by a disordered or incorrectly functioning organ, part, structure, or system of the body that occurs more frequently in the aged. Further, as used herein, a "degenerative disease" refers to a disease which is the result of a continuous process based on degenerative cell changes, affecting tissues or organs, which will increasingly deteriorate over time.

In the light of the present invention, age-related and/or degenerative diseases include, but are not limited to immune diseases, endocrine and metabolic diseases, diseases of the circulatory system, arthropathies, diseases of the digestive system, diseases of the neuro-musculoskeletal system including sarcopenia and frailty. Immune diseases are selected from the group comprising age-related immune dysfunction, age-related reduced immune response, such as for example reduced immune response to vaccination), bacterial infectious diseases, viral infectious diseases. Endocrine and metabolic diseases are selected from the group comprising obesity, metabolic syndrome, type II diabetes and progeria. Diseases of the circulatory system are selected from the group comprising atherosclerosis, ischemic heart disease, peripheral artery disease, and strike. Arthropathies are selected from the group comprising rheumatoid arthritis and osteoarthritis. Diseases of the digestive system are selected from the group comprising gastritis, peptic ulcer disease, inflammatory liver disease, digestive tract disorders, and constipation. Diseases of the neuromusculoskeletal system are selected from the group comprising extrapyramidal and movement disorders, diseases of myoneural junction and muscle, systemic atrophies primarily affecting the central nervous system, muscular dystrophy, duchenne muscular dystrophy, spinal muscular atrophy and related diseases, motor neuron diseases such as amyotrophic lateral sclerosis, abnormal involuntary movements, abnormalities of gait and mobility, ataxia, mitochondrial associated diseases, and sarcopenia.

Diseases of mitochondrial dysfunction are implicated in neurodegenerative, neoplastic, endocrine and cardiovascular diseases. In the present invention, age-related and/or degenerative mitochondrial associated diseases are diseases associated with impaired or disturbed functioning of the mitochondria, in particular leading to neuro-musculoskeletal dysfunctions. Said diseases are selected from central core disease and Optic Atrophy 1 (OPA1) associated diseases. Central core disease is an inherited neuromuscular disorder associated with impaired mitochondrial function. The disease is characterized by areas with reduced oxidative activity running along the longitudinal axis of the muscle fibre ("central cores"), and clinical features of a congenital myopathy. OPA 1 is located in the inner mitochondrial membrane and helps to regulate mitochondrial stability and energy output. Mutations in the OPA1 gene have been associated with optic atrophy type 1, which is a dominantly inherited optic neuropathy resulting in progressive loss of visual acuity leading in many cases to blindness.

As used herein "sarcopenia" means a loss of skeletal muscle mass, quality, and strength. Sarcopenia may lead to frailty, for example, in the elderly.

The term "frailty" refers to an adverse, primarily gerontologic, health condition, which can include low functional reserve, accelerated osteoporosis, easy tiring, decreased muscle strength, high susceptibility to disease and decreased libido (e.g. see Bandeen-Roch et al, The Journals of Gerontology Series A: Biological Sciences and Medical Sciences 61: 262-266, 2006). Frailty can be characterized by meeting three of the following five attributes: unintentional weight loss, muscle weakness, slow walking speed, exhaustion, and low physical activity. Further, reduction in frailty or stabilization of worsening of frailty is characterized by one or more of the following parameters: increased strength, stabilisation of strength loss, increase in lean body mass, stabilisation of weight loss, improved mobility, stabilisation of mobility reduction, increased energy, stabilisation of energy loss, increased levels of activity, stabilisation of activity loss, increased endurance, stabilisation of endurance loss, enhanced behavioural response to a sensory cue, stabilisation of a behavioural response to a sensory cue, a decrease or stabilisation in one or more inflammatory markers or biomarkers, an improvement in glucose homeostasis and metabolic or katabolic state, an improvement in neurotransmission or neuromuscular transmission, and a decrease in one or more biomarkers of clotting activation, wherein the reduction or stabilisation is relative to the condition of the subject before administration of the pharmaceutical combination or relative to a control population.

The present invention is further directed to the use of a pharmaceutical combination for prevention, stabilization and/or reduction of age-related complaints and/or degenerative complaints. These are selected from the group comprising muscular weakness, decreased muscular strength, neuromuscular degeneration, impaired mobility, impaired immune response, metabolic imbalance, general weakness, frailty.

As used herein, the term "muscular weakness" refers to a condition in which the strength of one or more muscles is reduced. The term "muscle strength" refers to the ability of a muscle or a group of muscles to produce tension or exert force through the skeletal system.

The term "skeletal muscle" includes skeletal muscle tissue as well as components thereof, such as skeletal muscle fibers (i.e., fast or slow skeletal muscle fibers), the myofibrils comprising the skeletal muscle fibers, the skeletal sarcomere which comprises the myofibrils, and the various components of the skeletal sarcomere described above.

The term "neuro-muscular degeneration" refers to any degeneration that affects any part of the nerves and/or muscles.

The term "impaired mobility" refers to impaired physical mobility and refers to any limitation in independent, purposeful physical movement of the body or of one or more extremities of the body.

In the light of the present invention, "impaired immune response" refers to reduced immunological reaction, be it cellular and/or humoral, of the body to pathogens, including bacteria and viruses, or cancer.

As used herein, "metabolic imbalance" refers to any condition that is associated with an elevated level of plasma glucose or plasma lipids.

The term "general weakness" refers to the state or condition of being weak, including the symptoms of fatigue, muscle weakness and having functional limitations.

As used herein, the term "degenerative complaints" is used for any discomfort or complaints that will eventually result in a degenerative disease.

As used herein, the term "inhibiting the development" or the term "delay in onset" of a sign of aging means delaying the onset, slowing the progression, or reducing the manifestation, of a sign of aging.

As used herein, the term "improving performance" refers to any aspect of performance, including cognitive performance or physical performance, such as, but not limited to, the ability of be self-sufficient, to take care of (some but not necessarily all) personal needs, to be ambulatory or otherwise mobile, or interaction with others.

Further, the present invention is directed to the use of a pharmaceutical combination according to the invention for improving a measure of life span and/or health span. The term "life span" as used herein refers to the maximum life span observed in a group of individuals. Alternatively, life span also refers to the average life span expected in a group of individuals.

The term "health span" refers to the period of time during which an individual meets one or more selected measures of health span. An increase in "health span" refers to an extension in the period of health, according to such measures, as compared to the period of health in a control population. An increase in health span can be measured, e.g., by determining the length of time that an individual continues to meet the selected measure(s) of health span. Alternatively, an increase health span can be determined by measuring a degree of improvement in one or more selected measures of health span that is correlated with an increase in the length of time that an individual continues to meet the selected measures of health span. Alternatively, health span is the period of life during which an individual is fully functional and free of chronic illness.

As used herein, a "control population" refers to a population that has not been treated with the combination according to the present invention, wherein the members of that population have one or more characteristics and/or conditions of a subject being treated with the combination of the present invention. Thus, for example, if a subject is being treated for frailty, the relevant control population would have frailty; and if a subject is being treated for any age-related disease, the relevant control population would have the same age-related disease.

The term "inflammatory marker" refers to an endogenous condition, often the presence, level, and/or form of a molecule, that indicates the presence of inflammation. For example, C-reactive protein (CRP) is an inflammatory marker that has been shown to predict future cardiovascular events in individuals with and without established cardiovascular disease. Inflammatory markers implicated in the inflammatory process leading to atherothrombosis, include for example CRP, adiponectin, monocyte chemoattractant protein 1 (MCP-1), CD40 ligand, and lipoprotein-associated phospholipase A(2) (Lp-PLA(2)).

The term "glucose homeostasis" refers to the state of, or tendency towards, normal (non-pathological) glucose levels, which vary appropriately in response to various stimuli. Illustrative measure of glucose homeostasis includes meal-stimulated insulin, glucose, and glucagon-like peptide-1 (GLP-1) levels.

The term "biomarker" of clotting activation" refers to an endogenous condition, often the presence, level, and/or form of a molecule, that indicates activation of the pathway leading to the formation of a blood clot. Illustrative biomarkers of clotting activation include, for example, prothrombin fragments 1 and 2, thrombin-anti-thrombin complex, and fibrin degradation products.

The term "immunosenescence" refers to the gradual deterioration of the immune system brought on by natural aging. It involves both the subject's capacity to respond to infections and the development of long-term immune memory, especially by vaccination. For example, immunosenescence includes the reduced vaccination response in aging people.

The term "subject" as used herein, refers to an animal, such as a mammal, for example a human, that has been or will be the object of treatment, observation or experiment. The methods described herein can be useful in both human therapy and veterinary applications. In some embodiments, the subject is a mammal, and in some further embodiments, the subject is a human. In a preferred embodiment, the subject is a human subject. In an even more preferred embodiment, the subject is a human subject with an age-related disease, for example a human subject with an age-related disease above 50 years. In another embodiment, the subject is a human subject with a degenerative disease. In still another embodiment, the subject is a human subject with an age-related disease and degenerative disease.

In all different embodiments of the present invention, the pharmaceutical combination according to the invention can be administered in a therapeutic or subtherapeutic daily dose to a subject, in particular a human subject.

The term "subtherapeutic dose" when used to describe the amount of the biguanide and/or acetylcholinesterase inhibitor refers to a dose of said compounds that does not give the desired therapeutic effect for the disease being treated when administered alone to a patient. This can also be referred to as "synergistically effective amount", referring to the synergy observed when administering the compounds together.

In one embodiment, the amount of biguanide or the acetylcholinesterase inhibitor administered is about 20% less than the therapeutically effective amount. In one embodiment, the amount of biguanide or acetylcholinesterase inhibitor administered is about 50% less than the therapeutically effective amount. Alternatively, the amount of biguanide or acetylcholinesterase inhibitor administered is about 25%, 30%, 35%, 40%, 45%, 50%, 55%, 60%, 65%, 70%, 75%, 80%, or 90% less than the therapeutically effective amount.

For example, a therapeutically effective amount of metformin, depending on the patient and/or condition, such as body weight, can be about 2000 mg/day or about 2500 mg/day. Accordingly, the aggregate subtherapeutic daily dose of metformin for a human patient is than about 400 mg/day or about 500 mg/day. In another embodiment, the aggregate subtherapeutic daily dose for a human patient is than about 1000 mg/day or about 1250 mg/day.

Also for example, a therapeutically effective amount of galantamine, depending on the patient and/or condition, such as body weight, can be about 16 mg/day or about 24 mg/day. Accordingly, the aggregate subtherapeutic daily dose of galantamine for a human patient is than about 3.20 mg/day or about 4.80 mg/day. In another embodiment, the aggregate subtherapeutic daily dose for a human patient is than about 8 mg/day or about 12 mg/day.

The present invention relates to a pharmaceutical combination comprising two different compounds. In this context, different ways of analysis of pharmacological effects of two (or more) compounds are available and widely accepted in the field. For example, the term "synergistic effects" refers to the phenomenon where the effect size of combination is larger than the sum of the individual effects. As this definition is very stringent, particularly given the biological variability, the highest single agent (HSA) model will be applied (Borisy, PNAS, 2013). According to this model, drug combinations are considered synergistic if the combinatorial effect is significantly larger than the largest effect of any of the single drugs at the same concentration as in the mixture. In the context of the present invention, synergistic effects of the pharmaceutical combination of the present invention are considered to be relevant and resulting in physiological effects.

In the experimental part of this invention, the inventors used the *C. elegans* a model organism for studying aging (Carretero et al., Curr Top Med Chem 2017; Kenyon, Nature 2010). *Caenorhabditis elegans* is a small nematode that has become one of the most intensively studied models in biological research. Since the second half of the 20th century, many fundamental discoveries in life sciences were made in this nematode, including the discovery of life span-promoting genetic pathways. These pathways have remained relatively unchanged during evolution, allowing for their dissection in a simple invertebrate such as *C. elegans*. Several changes that take place during aging in *C. elegans* are shared with aging in humans, including decreased skin elasticity, a reduction in muscle mass, loss of muscle integrity, loss of motility and increased susceptibility to infections. Additionally, multiple forms of learning and memory decline with age, both in *C. elegans* and mammals. Also the major genetic and biochemical networks that underlie aging and age-related disease seem evolutionarily well-conserved. Hence, amenable model organisms such as *C. elegans* allow for a relatively streamlined and high-throughput approach to study and understand these phenomena. Currently, *C. elegans* is being utilized by researchers worldwide to decipher evolutionarily conserved signaling pathways involved in longevity, and to assess the therapeutic potential of interventions aimed at alleviating human aging. In essence, *C. elegans* combines the experimental advantages of micro-organisms (i.e. ease of handling and experimental manipulation) with the benefits of a multicellular context (i.e. modeling of complex processes such as organismal aging, pathogenesis and behavior).

The most common method for measurement of *C. elegans* aging is based on manual inspection of worm survival on bacteria-coated agar plates.

Further, a muscle-specific optic atrophy 1 (OPA1) mouse model was used in the examples as shown below. This transgenic mouse model effectively recapitulates key pathophysiological aspects of sarcopenia-related muscle loss and strength, and show precocious aging (e.g. white hair, kyphosis). OPA1 deletion specifically in skeletal muscle results in mitochondrial dysfunction, increased oxidative stress and inflammation. Moreover, the OPA1 mouse model is a recognized mouse model for mitochondrial associated diseases related to OPA1, such as optic atrophy and hypertension cause by optic atrophy (Archer, 2013, New Engl J Med 369: 23).

EXAMPLES

Example 1: *Caenorhabditis elegans* Model

Materials and Methods

Chemicals of Interest

Galantamine hydrobromide (Gal; CAS 1953-04-4, reference PHR1623), donepezil hydrochloride (Don; CAS 120011-70-3, reference PHR1584), memantine hydrochloride (Mem; CAS 41100-52-1, reference PHR1886) and 1,1-Dimethylbiguanide hydrochloride (Met; CAS 1115-70-4, reference D150959) were purchased from Sigma-Aldrich (Saint Louis, USA). Rivastigmine tartrate (Riv; CAS 129101-54-8, reference A18484M) was supplied by Interquim S.A. (Barcelona, Spain). Stock solutions were prepared in ultrapure Milli-Q water at 3.8 mg/ml (Gal), 416 mg/ml (Don), 216 mg/ml (Mem), and 100 mg/ml (Riv).

Life Span Assays Using *Caenorhabditis elegans*

The wild-type *C. elegans* N2 strain was obtained from the *Caenorhabditis* Genetic Center (University of Minnesota, USA) and was cultivated at 20° C. on standard nematode growth medium (NGM) seeded with a thin layer of *Escherichia coli* OP50, unless stated otherwise. Life span of *C. elegans* was measured analogous to methods described earlier[1,2]. The first day of adulthood was always recorded as day 0. FUdR (5-fluoro-2'-deoxyuridine, Sigma-Aldrich) was used in all life span assays to avoid progeny production. Multiple independent assays were carried out. A minimum of 100 animals per condition per assay was used, as to ensure sufficient statistical power.

During the 'single dosing assay', we used the WorMotel platform for long-term recurrent imaging of *C. elegans*[3]. This semi-automated platform allows for unbiased longitudinal monitoring of *C. elegans* aging phenotypes, including daily measurements of survival as well as locomotion quantification. From the onset of adulthood, animals were confined to individual wells in screening plates (i.e. microfabricated WorMotel chips prepared as described in[3]) that were seeded with *E. coli* HT115(DE3) as a food source and supplemented with the corresponding compounds at different doses (Table 1). Four replicate screening plates were assayed, with all four tested conditions present on each screening plate (in randomized locations). Animals were kept on the same screening plates for the duration of the experiment (i.e. 30 days). The time of death is determined as the final time of nonzero movement. Note that this imaging platform is incompatible with repeated dosing. We used the statistical software R to construct Kaplan-Meier survival curves, calculate mean and median life span and carry out all related statistical analyses. To compare survival between two conditions, log-rank tests were used (i.e. survdiff function of the survival package, adjusted for multiple comparisons via the Benjamini-Hochberg method). The corresponding p-values are referred to as $p_{log-rank}$.

During the 'repeated dosing assay', we followed the standard method in the field (i.e. manual inspection of survival of age-synchronized populations on bacteria-coated agar plates[2]), which is robust and technically relatively simple. In short, at the onset of adulthood, animals were transferred to standard NGM assay plates (untreated control) or NGM assay plates supplemented with the corresponding compounds at different doses (Table 1). Animals were transferred to fresh standard NGM assay plates or fresh NGM assay plates supplemented with the corresponding compounds at different doses thrice in the first week and weekly thereafter (for a total duration of 33 days). This dosing schedule is in accordance with standardized protocols from the *Caenorhabditis* Intervention Testing Program (CITP)[4]. Met was added to the NGM prior to autoclaving, whereas Gal was pipetted onto the seeded assay plates (at least two hours prior to transferring animals on to the assay plates). A same volume of liquid was added to all plates, also to plates of the untreated control and Met condition (i.e. mock treatment). Animals that crawled off the assay plates or died of internal hatching were censored. The number of live and dead worms was scored every one to two days.

Locomotion Assay

Locomotion of *C. elegans* is characterized by sinusoidal movements (i.e. body bends), and progressively diminishes during adult life. As in other animals, maintenance of coordinated movement is considered a prime health span parameter[5]. More specifically, maximal locomotor activity is a good proxy for *C. elegans*' general fitness and health[6], whereas the rate of decline in locomotor activity in mid-life has been shown to predict ultimate life span[7].

A. WorMotel-Based Locomotion Tracking (Single Dosing)

Each imaging period, the mean and maximum locomotion activity before and after a blue light stimulus are quantified (as described in[3]). The resulting activity values are termed 'baseline locomotion' and 'stimulated locomotion', respectively. Highly mobile animals yield high activity values, whereas slowly moving or older animals yield low activity values. 'Mean activity' of an animal, represents the average of locomotion activity values that were detected for that animal over the entire experiment duration. 'Maximal activity' represents the highest maximum locomotion activity value detected for an animal, irrespective of the day of detection. 'Healthy days' is defined as the total number of days of which the activity of a living animal was observed to be larger than 15% of the mean maximal activity of the untreated control condition present on the same technical replicate (i.e. chip). An increase in 'healthy days' is indicative for an increase in locomotion-based healthspan. Results were analyzed using one-way and two-way ANOVAs, with the Holm-Sidak correction for multiple comparisons in GraphPad Prism software. All corresponding p-values are referred to as $p_{ANOVA}$.

B. Camera-Based Locomotion Tracking (Repeated Dosing)

To quantify locomotion effects in more detail, we utilized an automated tracking system for *C. elegans* that is compatible with standard petri plates. The multi-camera tracking system allows for objective quantification of mean locomotion speed, maximal locomotion speed and multiple behavioral parameters via path-based image analysis. The system was utilized similar to Peymen et al[8]. Two distinct assays were performed. In a first assay (Table 2), the locomotion effects of Gal, Met and a combination of both compounds was assayed. This allowed to test for synergetic effects between Gal and Met on multiple locomotion parameters. In a second assay (Table 3), we characterized the locomotion effects of the combination of Met with different acetylcholinesterase inhibitors (i.e. Gal, Don and Riv), as well as the combination of Met with the acetylcholinesterase inhibitor-like compound Mem. As such, we were able to test whether there is a class effect of acetylcholinesterase inhibitors as a whole (in combination with Met). Synchronized wild-type animals were grown in the presence of the corresponding compounds at different doses from the L4 stage (i.e. day 0) and FUdR, until the start of the measurement. Animals were re-dosed thrice (at day 2, 4 and 7) via transfer to fresh compound-treated NGM plates. Prior to imaging, for each replicate 20 well-fed living animals were manually transferred from their culture plate to an unseeded NGM plate, and after 5 min transferred to another unseeded NGM plate used for imaging. Image acquisition took place with StreamPix 6 multicamera software (GigE PRO GP11004M camera with KOWA LM16JC10M lens) for 11 min at 2 fps and a constant exposure, after which worms were tracked using custom particle-tracking MATLAB code. For each mobile animal (i.e. an animal that moved for at least 2 min during the imaging period), both mean and maximal locomotion speeds were extracted, as well as the behavioral metrics 'cell occupancy' and 'fraction running'. The latter represents the fraction of time that an animal was detected to be running (as opposed to pausing or turning). Cell occupancy is a metric quantifying the spatial search efficiency of a worm. Cell occupancy values represent the number of unique cells (squares of 1 mm$^2$) that the worm visited during the imaging period. Both behavioral parameters decline during aging. Experiments were performed in triplicate (or quadruplicate), with 20 worms per condition per replicate. The results were analyzed using multiple t testing, with the Holm-Sidak correction for multiple comparisons, in GraphPad Prism software. The corresponding p-values are referred to as p.

In Vivo Gene Activity Assays

The transparent body of *C. elegans* allows for straightforward and non-invasive measurements of in vivo gene transcription via transgenic fluorescent reporters[9]. We measured transcription of the gst-4$_p$.: GFP *C. elegans* GFP reporter to gain insight into the intracellular signaling networks that are affected by Met and/or Gal. Additionally, we tested whether Met and Gal have a synergistic or potentiating effect on activation of gst-4 gene transcription.

The gst-4 gene encodes for the cytoprotective and drug-metabolizing enzyme glutathione S-transferase 4 (GST-4). Gst-4 is a direct target of SKN-1, an ortholog of the mammalian Nuclear Factor E2-Related Factor (Nrf2) protein family that is a key transcription factor involved in the protection against oxidative and xenobiotic stresses. In response to oxidative insults, SKN-1/Nrf2 is phosphorylated by PMK-1/p38 MAPK (among others) in the cytoplasm, after which it migrates to the nucleus to induce the expression of a wide range of antioxidant and detoxifying enzymes such as gst-4. In *C. elegans* aging research, transcriptional activation of gst-4 is often used as a read-out for SKN-1 activity. Nonetheless, it has been shown that gst-4 can also be transcriptionally activated by epidermal growth factor (EGF) signaling pathway via EOR-1, a BTB/zinc-finger transcription factor similar to mammalian promyelocytic leukemia zinc-finger protein (PLZF). Upregulation of detoxifying GST enzymes is a common feature of long-lived *C. elegans* and is linked to longevity not only in worms but across species, including humans[10]. GFP fluorescence was quantified using an automated method, as described earlier[11]. In short: JMET69 animals with genotype ls[gst-4 (1491 bp)::gfp;unc-119(+)];ls[unc-54$_p$::mCherry;unc-119 (+)] were grown in the presence and absence of drugs (i.e. Met and/or Gal) on NGM plates seeded with *E. coli* OP50, from the L1 until the late L4 stage, before transfer to a 96 well plate for fluorescence quantification. Background-corrected values are shown. No BCA normalization was used. Averages were statistically compared via a one-way ANOVA with Sidak's multiple comparison test in GraphPad Prism software. The corresponding p-values are referred to as $p_{ANOVA}$.

Quantifying Muscle Morphology and Deterioration in *C. elegans*

Progressive loss of muscle mass and function with aging in *C. elegans* shows a very similar progression as sarcopenia in humans[12]. Sarcomeres are fundamental muscle units, responsible for muscle contraction. *C. elegans*' sarcomeres consist of alternated filaments containing myosin and actin, similar to sarcomeres of vertebrates. While sarcomere myofilaments in the body wall of young animals are organized in parallel symmetric rows, sarcomere myofilaments in older animals become progressively disorganized with a more irregular shape and orientation. By using a transgenic reporter strain that has a fusion of myosin heavy chain with fluorescent GFP (strain RW1596; myo-3p:MYO-3::GFP), muscle structure of *C. elegans* can be visualized in vivo. Combined with confocal microscopy and bioinformatic analysis this offers not only qualitative, but also quantitative readouts for the assessment of the organizational level of muscle fibers. An analytical method to quantify muscle deterioration has been optimized at the laboratory of Prof. Bart Braeckman (UGent; unpublished data). We used this technique to verify whether animals treated with Gal and/or Met, display a muscle phenotype resembling that of younger untreated individuals.

Synchronized RW1596 animals were grown in the presence of the corresponding compounds at different doses (see FIG. 7A and FIG. 7B) and FUdR, from the L4 stage (i.e. day 0) onwards. Animals were re-dosed once, at day 7, via transfer to freshly compound-treated NGM plates. Measurements were performed at late adulthood (i.e. day 14), using at least 30 animals per condition.

For each animal, the two morphological metrics 'aspect ratio' and 'smoothness' were extracted. Aspect ratio is a measure for the general dimension (i.e. elongated shape) of a sarcomere. The higher this value, the more elongated the sarcomere is. The aspect ratio is calculated as the ratio of the length of the major axis (=length) and the length of the minor axis (=width) for individual myofilaments within a sarcomere. As the animals age, the aspect ratio declines. Smoothness is a measure for the smoothness of the myofilament contours. The lower this value, the more 'jagged' and 'deformed' the edge of a myofilament is. Smoothness is denoted in arbitrary units. A value of 1 corresponds to the maximal smoothness observed in muscle filaments (i.e. at early adulthood) whereas a value of 0 corresponds to the smoothness observed in very old (day 18) control worms. Two conditions were statistically compared via a two-tailed Student's t test, using GraphPad Prism software.

Results

Synergistic Effect of the Combination of Metformin and Galantamine on Lifespan Extension Single dosing of the individual compounds significantly increased survival of *C. elegans* compared to the untreated control (Met: $p_{log-rank}$=0.00215; Gal: $p_{log-rank}$=0.000176) (FIG. 1, Table 1). To test for drug synergy we used the higher single activity (HSA) model[13]. According to this model, drug combinations are considered synergistic if the combinatorial effect is significantly larger than the largest effect of any of the single drugs. Using this model, we uncovered drug synergy as treatment with 25 mM Met and 100 UM Gal resulted in a further increase in survival in comparison to the individual compounds (Met: $p_{log-rank}$=0.049; Gal: $p_{log-rank}$=0.0244) (FIG. 1).

Figure 2:
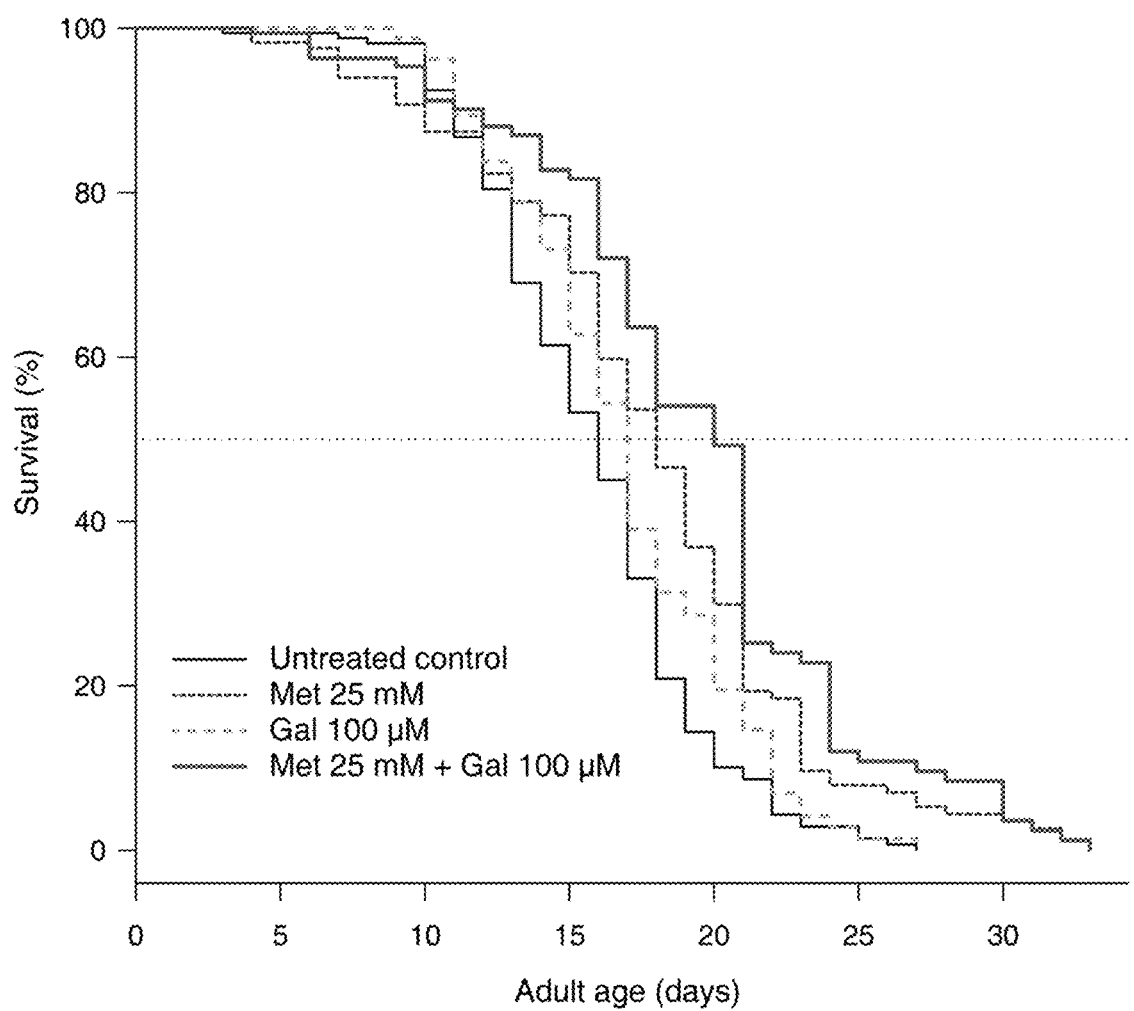
FIG. 2. Life span assay using *C. elegans* to evaluate the life-prolonging effect of repeated dosing of metformin, galantamine and the combination of metformin and galantamine. Treatment started at the first day of adulthood and animals were repeatedly dosed. Full life span data are displayed in Table 1.

A stronger potentiating effect of the combination Met and Gal was observed for animals that were repeatedly dosed with Met and Gal (FIG. 2, Table 1). Again, the combination of both drugs (Met and Gal) induced the strongest life span extension: mean life span increased with 22.1% compared to the untreated control ($p_{log-rank}$<1E-6), with 12.5% compared to the Gal-treated group ($p_{log-rank}$=0.000006) and with 8.3% compared to the 25 mM Met-treated group ($p_{log-rank}$=0.037). Maximum lifespan of animals treated with the Gal and Met combination increased with 29% compared to the untreated control, with 23% compared to the Gal-treated group and with 17% compared to the Met-treated group. Overall, the Met and Gal drug combination induced significantly greater effects on survival than the largest effect produced by any of its individual components (Table 1), indicative of a synergetic effect between Met and Gal.

and Gal, in comparison to at least one of the single compound treatments (FIG. 3A-FIG. 3C). None of the single compounds induced a significant better effect than the combination of Gal and Met, hinting at improved efficacy when both Gal and Met are combined.

In comparison to the untreated control, the combination of Gal and Met increased the total number of healthy days (i.e. locomotion-based health span) by 30%, which was significantly better than the effect observed for Met (+14%, $p_{ANOVA}$=0.037) but not significantly different than the effect observed for Gal (+20%, $p_{ANOVA}$=0.095) (FIG. 3C). In summary, locomotion activity during aging as well as locomotion-based health span (i.e. the period of life that an animal display healthy levels of muscle function) is significantly enhanced in animals treated with the combination of Met and Gal.

Repeated Dosing of C. elegans with the Combination of Galantamine and Metformin Positively Impacts Locomotion and Behavioral Parameters in a Synergetic Manner To gain more insight into the effects on locomotion-based health span, we quantified four locomotion and behavioral parameters in post-reproductive C. elegans adults following repeated dosing with Gal, Met, and the combination. The highest levels for all four parameters (i.e. resembling locomotion phenotypes of younger individuals) were observed for animals treated with the combination of 25 mM Met and

TABLE 1

Detailed survival data obtained from the life span assays using C. elegans. Treatment with Met, Gal as well as with a combination of Met and Gal, significantly enhances survival of adult C. elegans. Pooled data of multiple assays are shown. N the total number of observed deaths for each condition, SEM the standard error of the mean, LS life span, MLS mean life span, * $p_{log-rank}$ < 0.05,  $p_{log-rank}$ < 0.01, * $p_{log-rank}$ < 0.001, **** $p_{log-rank}$ < 0.0001. Median lifespan (Median LS) is defined as the day on which 50% of the animals are still alive (i.e. 50th quantile of the survival curve). Maximum lifespan (Max LS) is defined as the day on which 10% of the animals are still alive (i.e. 90th quantile of the survival curve).

| Condition | [Gal] (μM) | [Met] (mM) | MLS ± SEM (days) | Median LS (days) | Max LS (days) | Increase MLS versus untreated control | Decrease MLS versus combo Met25 + Gal100 | N |
|---|---|---|---|---|---|---|---|---|
| Single dosing | | | | | | | | |
| Untreated | 0 | 0 | 17.41 ± 0.44 | 18 | 25 | | −14.8% **** | 170 |
| Gal 100 | 100 | 0 | 19.63 ± 0.44 | 20 | 27 | +12.8% *** | −3.9% * | 183 |
| Met 25 | 0 | 25 | 19.08 ± 0.58 | 20 | 28 | +9.6% ** | −6.7% * | 127 |
| Met 25 + Gal 100 | 100 | 25 | 20.44 ± 0.52 | 21 | 29 | +17.5% **** | | 153 |
| Repeated dosing | | | | | | | | |
| Untreated | 0 | 0 | 15.80 ± 0.31 | 16 | 21 | | −18.1% **** | 148 |
| Gal 100 | 100 | 0 | 16.87 ± 0.32 | 17 | 22 | +6.8% * | −12.5% **** | 149 |
| Met 25 | 0 | 25 | 17.68 ± 0.50 | 18 | 23 | +11.9% **** | − 8.3% | 116 |
| Met 25 + Gal 100 | 100 | 25 | 19.29 ± 0.57 | 20 | 27 | +22.1% *** | | 87 |

Single Dosing of C. elegans with the Combination of Galantamine and Metformin Positively Impacts Locomotion and Locomotion-Based Healthspan A single treatment of C. elegans with the individual compounds (Gal and Met) significantly increased multiple locomotion activity parameters during adulthood (FIGS. 3A-FIG. 3C). For example, Gal significantly increased maximal baseline activity by 15% ($p_{ANOVA}$=0.0054) while Met increased maximal baseline activity by 35% ($p_{ANOVA}$<0.0001) compared to the untreated control. The combination of Gal and Met induced the biggest percentual increase in maximal baseline activity: 41% compared to the untreated control ($p_{ANOVA}$<0.0001). Moreover, for most locomotion parameters a significant improved effect was observed for animals treated with the combination of Met 100 UM Gal (Table 2, FIG. 4A-FIG. 4D). In animals treated with this Met and Gal combination, mean locomotion speed increased by 141% (p<0.000001), maximal speed by 24% (p<0.001), the fraction of time spent running by 46% (p<0.000001) and cell occupancy by 239% (p<0.000001) compared to the untreated control. In essence, the age-related decline of these four locomotion-based parameters is significantly mitigated by the combination of Met and Gal. Moreover, significant synergetic effect between Met and Gal was observed for the parameters 'mean locomotion speed' and 'cell occupancy' in comparison to the single compound treatments (Table 2, FIG. 4A and FIG. 4D). Taken together, our results indicate that the combination of Met and Gal is capable of improving locomotion-based health span more so than Met or Gal alone.

Next, to evaluate the breadth of our compound mixture strategy, we assayed locomotion of *C. elegans* animals treated with other members of the acetylcholinesterase inhibitor group (always in combination with Met). The combination of 25 mM Met with other acetylcholinesterase inhibitors (i.e. Don and Riv) or acetylcholinesterase inhibitor-like compounds (i.e. Mem) induced a similar locomotion phenotype as the combination of 25 mM Met with the acetylcholinesterase inhibitor Gal (FIG. 5A-FIG. 5D, Table 3). When considering all four tested conditions (Table 3), there was essentially no significant difference between the compound treatments ($p_{ANOVA}$=0.25). Out of the 16 performed statistical comparisons (i.e. multiple t tests), only one was significant: when Mem was combined with Met, maximal locomotion speed decreased (−14.5%; p=0.0036), compared to the condition wherein Met was combined with Gal (Table 3). Nonetheless, all 15 other statistical comparisons of locomotion and behavioral parameters were found to be not significantly different (FIG. 5A-FIG. 5D). Hence, when combined with Met, all tested acetylcholinesterase inhibitors appear to act in a similar fashion.

Glutathione S-Transferase 4 Transcription is Increased by Gal and Met in a Synergetic Fashion We assayed glutathione S-transferase 4 (gst-4) transcription levels of age-synchronized *C. elegans* populations, following drug treatment. As expected from literature[14], animals treated with Met displayed significant higher gst-4 transcription levels (+26%, $p_{ANOVA}$<0.0001, FIG. 6) compared to the untreated control. Treatment with solely 100 UM Gal induced no significant increase in gst-4 transcription (+9%, $p_{ANOVA}$=0.37). Yet, the combination of 25 mM Met and 100 μM Gal induced the strongest activation of gst-4 transcription. The fluorescent signal increased with 62% compared to 100 UM Gal ($p_{ANOVA}$<0.0001) and with 28% compared to treatment with solely 25 mM Met ($p_{ANOVA}$<0.0001). Hence, we found that Gal and Met act synergistically to activate gst-4 transcription. This effect was highly consistent and robustly observed in additional independent assays, both in the presence and absence of oxidative stress (data not shown). Activation of gst-4 is indicative of enhanced protection against oxidative stress and xenobiotics (detoxification), as well as activation of the pro-

TABLE 2

Locomotion of mid-adult *C. elegans* (i.e. day 7 post-reproductive adults) is significantly enhanced following repeated dosing with Gal and Met, as well as with a combination of both. Pooled data of multiple replicates is shown.
Significant synergetic effects between Gal and Met (according to the HSA model definition) are indicated in bold.
Significance (versus the untreated control condition) is indicated via: $^{NS}$ not significant, * p < 0.05,  p < 0.01, * p < 0.001.
N the total amount of tested animals, SEM the standard error of the mean, # the number of replicate assays performed.
Fraction running represents the fraction of time that an animal spent running (as opposed to pausing or turning).
Cell occupancy indicates the number of unique cells (squares of 1 mm²) that a worm visited during the imaging period.
Data corresponds to FIG. 4.

| Assays | Condition | [Gal] (μM) | [Met] (mM) | Mean speed (μm/s) ± SEM | Maximal speed (μm/s) ± SEM | Fraction running (%) ± SEM | Cell occupancy (unique areas visited) ± SEM | N | # |
|---|---|---|---|---|---|---|---|---|---|
| Met + Gal | | | | | | | | | |
| | Untreated | 0 | 0 | 50 ± 3 | 242 ± 13 | 48 ± 2 | 11 ± 1 | 60 | 3 |
| | Gal 100 | 100 | 0 | 48 ± 4 $^{NS}$ | 270 ± 17 $^{NS}$ | 48 ± 2 $^{NS}$ | 11 ± 1 $^{NS}$ | 80 | 4 |
| | Met 25 | 0 | 25 | 102 ± 5 *** | 262 ± 8 $^{NS}$ | 67 ± 2 *** | 28 ± 3 *** | 60 | 3 |
| | Met 25 + Gal 100 | 100 | 25 | 120 ± 6 *** | 299 ± 8 *** | 70 ± 2 *** | 37 ± 3 *** | 60 | 3 |
| | Significant synergy between Gal and Met? | | | Yes | No | No | Yes | | |
| | $p_{Met\ 25\ +\ Gal\ 100\ versus\ Gal\ 100}$ | | | p < 1E−6 | p = 0.14 | p < 1E−6 | p < 1E−6 | | |
| | $p_{Met\ 25\ +\ Gal\ 100\ versus\ Met\ 25}$ | | | p = 0.046 | p = 0.0092 | p = 0.17 | p = 0.037 | | |

TABLE 3

Combining Met with different acetylcholinesterase inhibitors (i.e. Don, Riv and Gal) or acetylcholinesterase inhibitor-like compounds (i.e. Mem), results in similar locomotion phenotypes. Significance (versus the Met 25 + Gal 100 condition) is indicated via: $^{NS}$ not significant, * p < 0.05. Locomotion was quantified at day 7 of adulthood, similar to the data presented in Table 2. Pooled data of multiple replicates is shown. N the total amount of tested animals, SEM the standard error of the mean, # the number of replicate assays performed. The final concentrations of Gal (100 μM), Don (80.92 μM), Riv (57.12 μM) and Mem (132.2 μM) are based on their maximal daily clinical dosages. Data corresponds to FIG. 5.

| Assays | Condition | Mean speed (μm/s) ± SEM | Maximal speed (μm/s) ± SEM | Fraction running (%) ± SEM | Cell occupancy (unique areas visited) ± SEM | N | # |
|---|---|---|---|---|---|---|---|
| Met (mM) + other AChEI (μM) | | | | | | | |
| | Met 25 + Gal 100 | 126 ± 5 | 375 ± 10 | 69 ± 1 | 29 ± 2 | 80 | 4 |
| | Met 25 + Don 80.9 | 127 ± 6 $^{NS}$ | 374 ± 11 $^{NS}$ | 65 ± 1 $^{NS}$ | 31 ± 3 $^{NS}$ | 60 | 3 |
| | Met 25 + Riv 57.1 | 126 ± 2 $^{NS}$ | 342 ± 9 $^{NS}$ | 69 ± 2 $^{NS}$ | 25 ± 2 $^{NS}$ | 60 | 3 |
| | Met 25 + Mem 132.2 | 116 ± 9 $^{NS}$ | 321 ± 13 * | 64 ± 2 $^{NS}$ | 30 ± 3 $^{NS}$ | 60 | 3 | longevity transcription factors Nrf2/SKN-1 and/or PLZF/EOR-1. As noted previously, upregulation of GST enzymes is linked to longevity in multiple species (including humans) and is a common feature of long-lived *C. elegans*. Hence, the synergetic activation of gst-4 is in line with our previous observations of a synergetic effect between Gal and Met on longevity. Therefore, as gst-4 activation protects against oxidative stress, we will investigate the effect of the combination of Gal and Met on stress resistance to heat and oxidative stress using the label-free automated survival scoring method (FLASS), a method to automate survival assays that uses death-associated fluorescence to determine median time of death, as previously described 15.

Muscle Morphology of *C. elegans* is Improved by a Combination of Gal and Met

*C. elegans* treated with a combination of Gal and Met display quantitative and qualitative improvements in muscle morphology at late adulthood, compared to animals of the untreated control condition (FIG. 7A and FIG. 7B). Compared to the untreated control, *C. elegans* treated with the combination of 25 mM Met and 100 UM Gal have a significantly increased sarcomere aspect ratio (+7.7%, p=0.045, FIG. 7A). Essentially, the general dimension of their sarcomeres (i.e. aspect ratio) resembles that of younger individuals. Treatment with solely 25 mM Met or with solely 100 UM Gal induced no significant increases in aspect ratio (FIG. 7A).

The other morphological muscle metric that was quantified was myofilament contour smoothness. Compared to the untreated control condition, we observed a 55% increase in myofilament contour smoothness for animals treated with a combination of 25 mM Met and 100 μM Gal (FIG. 7B). Yet, only a trend was observed (p=0.076), presumably due to higher biological variation for this parameter. Nonetheless, on representative microscopic images, it was noted that the myofilaments within the sarcomeres of animals treated with the combination of Gal and Met have a more regular shape and orientation than those of untreated animals. More specifically, myofilaments of animals treated with the combination of Gal and Met tend to be organized in parallel symmetric, in contrast to untreated animals whose myofilaments tend to have a somewhat more irregular shape and orientation. This suggests an improved muscle function in animals treated with a combination of Gal and Met, which is in agreement with our previous observation of enhanced locomotion rate in these animals (see above).

Example 2: Mouse Model

Introduction

Based on the evidence that the components metformin and galantamine target known pathways involved in aging and frailty, we investigated the effects of this combination on sarcopenia and muscle strength in the muscle-specific optic atrophy 1 (OPA1) mouse model as well as on overall change in aging parameters. This transgenic mouse model effectively recapitulates key pathophysiological aspects of sarcopenia-related muscle loss and strength and show precocious aging (e.g. white hairs, kyphosis)[16]. OPA1 deletion specifically in skeletal muscle results in mitochondrial dysfunction, increased oxidative stress, and inflammation.

Material and Methods

OPA1 Mouse Model

The generation and characterization of the Opa1$^{-/-}$ mice is described in detail elsewhere[16,17]. The inducible muscle-specific deletion of OPA1 was obtained by crossing the Opa1$^{fl/fl}$ line with mice carrying Cre-ER driven by human skeletal actin promotor (HSA). Tamoxifen-induced Cre-LoxP recombination was activated by oral administration of tamoxifen-containing chow (Tam400/Cre ER Harlan) which was provided ad libitum for 5 weeks. Animals with food intake received indicatively, 1 mg of tamoxifen per day. Experiments were performed on both female and male mice.

Diets

Muscle-specific OPA1 knockout were maintained on house chow (Standard Diet Certificate from Mucedola S.R.L.) or a house chow supplemented with both metformin and galantamine. The combination was formulated to provide daily doses of 2.5 mg galantamine and 410 mg metformin kg-1 bodyweight. The study diets were purchased from Mucedola S.R.L.

Preclinical Tests for Body Composition and Energetics

Changes in body composition occur throughout the human lifespan. Overall, early old age is associated with progressively increasing fat mass and decrease in lean body mass and bone mineral density, while at later stages in life, humans start to lose weight, in particular fat stores.

Body Weight and Body Composition

Body weight was monitored weekly or biweekly. Measurements of lean and fat mass in live mice were assessed by EchoMRI-100 (EchoMRI, Houston TX, USA).

Metabolic Assessment

Mouse metabolic rate was assessed by indirect calorimetry using the PhenoMaster metabolic cages system (TSE, Berlin, Germany), which provided direct measurements of oxygen consumption (VO2) and carbon dioxide production (VCO2). Based on these parameters, energy expenditure was calculated[18]. Moreover, food consumption was monitored.

Preclinical Tests for Neuromuscular Function and Performance

Neuromuscular function and performance are key clinical outcomes in assessment of overall health in elderly, as they are highly associated with adverse health events such as falls, depression, disability, and death.

Physical Performance

Functional decline among elderly people, often associated with a decline in motor and cognitive abilities and substantial morbidity, is considered a key health determinant in older adults. In mice, a battery of tests has been developed to assess behavioral outcomes in aging mice.

Treadmill. The concentric training protocol consisted of treadmill (Biological Instruments, LE 8710 Panlab Technology 2B) running to exhaustion, with a 5° decline constant at 13 cm/s. Total running time was recorded for each mouse.

Grip strength. Grip strength was performed by allowing mice to grab a grid and subsequently pulling the mice from the tail and recording the time until release.

In vivo force measurements were performed in living animals using a 305B muscle lever system (Aurora Scientific, ON, Canada) as described previously[19]. Briefly, the force/frequency protocol consisted of a series of stimulations at increasing frequencies (single pulse, 20 Hz, 40 Hz, 55 Hz, 75 Hz, 100 Hz and 150 Hz). Each stimulation is performed >30 seconds after the last, the applied voltage ranges from 4 to 6V, the duration of each train is set to 200 ms while the duration of each single pulse is set to 200 us.

Harvesting of Muscle Tissue, Liver and White Adipose Tissue 67 days after induction, mice were sacrificed and muscles (gastrocnemius, tibialis anterior, soleus) were collected using standardized dissection methods. Muscle tissues were cleaned of excess fat and connective tissue, weighed on an analytical balance, and collected for further analysis. Muscle tissue was preserved for histology and RNA. Liver was collected and preserved for histology. White adipose tissue was collected and weighed on an analytical balance.

Gene Expression

Total RNA was isolated from muscles using TRIzol (Invitrogen). Complementary DNA was generated using the SuperScript III Reverse Transcriptase (Invitrogen). Gene expression was determined by qPCR as described[16]. Quantitative PCR was performed with the following primers: IL6Fw: TAGTCCTTCCTACCCCAATTTCC; IL6Rv: TTGGTCCTTAGCCACTCCTTC GAPDHFw: CACCATCTTCCAGGAGCGAG; GAPDHRv: CCTTCTCCATGGTGGTGAAGAC.

Histology and Immunofluorescence

Cryosections of the gastrocnemius muscles and liver were stained for succinate dehydrogenase (SDH) and Oil red O staining, respectively. Total myofiber number of the gastrocnemius muscle was calculated from entire hindlimb cross-section based on assembled mosaic image (20× magnification). For immunostaining, antibody for NCAM (1:200 dilution in blocking buffer, Millipore, St. Louis, MO) was used. WGA conjugated to Cy3 was used to identify the sarcolemma. The images were captured using a Leica DFC300-FX digital charge-coupled device camera and the Leica DC Viewer software.

Statistical Methods and Synergy Definition

All data are presented as mean±SEM. Comparisons between 2 groups were done by 2-tailed Student's t tests. For statistical analyses of group differences, we performed a one-way ANOVA with appropriate correction for multiple comparisons (Tukey's multiple comparison tests, GraphPad Prism software). A repeated measures ANOVA was used to evaluate significant time-course changes between two (or more) groups. P values below 0.05 were considered significant.

Results

Figure 8F:
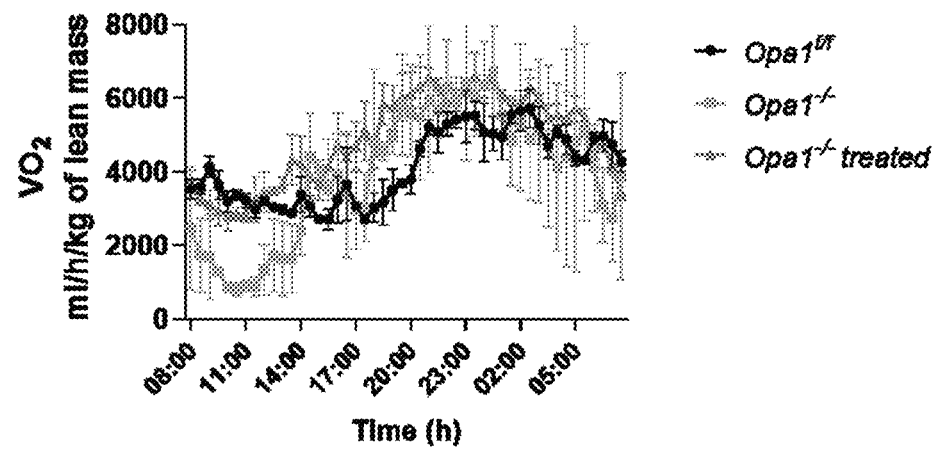
Figure 8G:
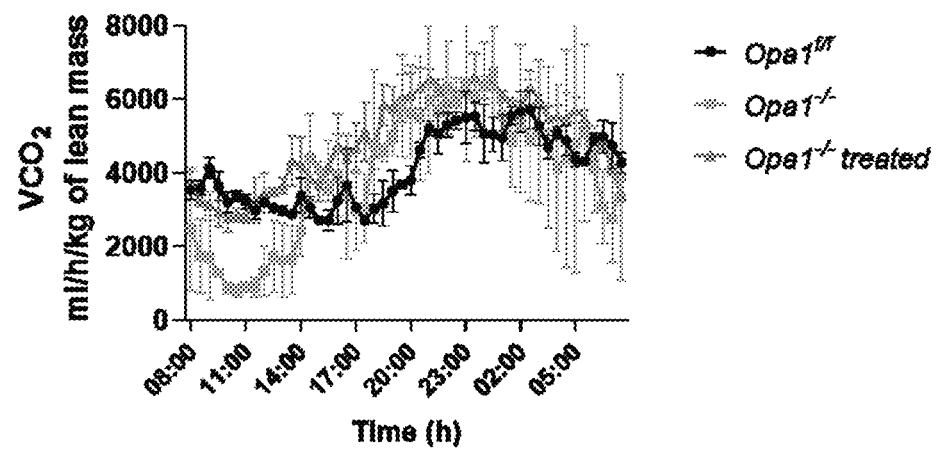
Figure 8H:
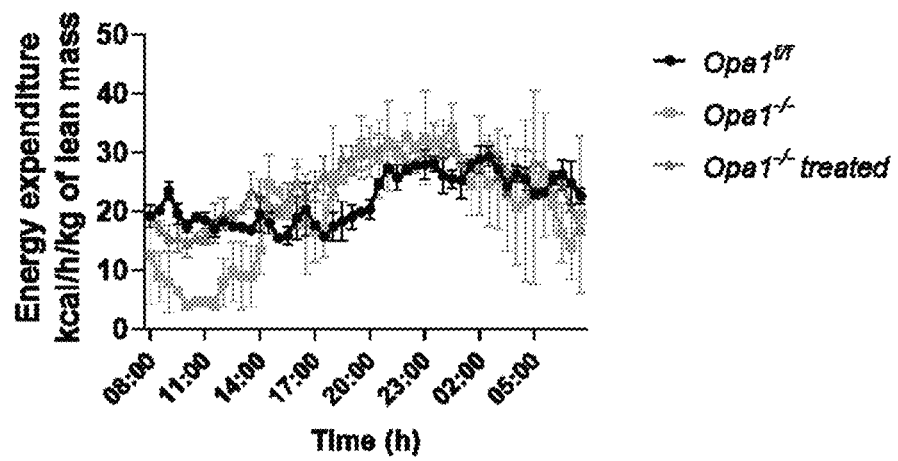
Figure 8I:
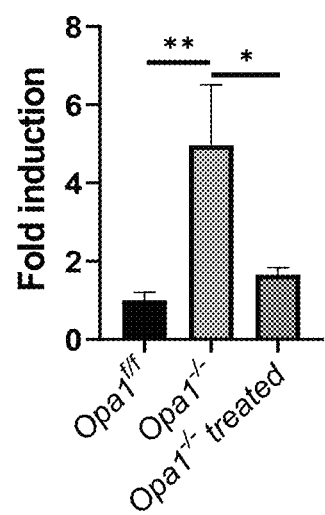

Muscle Specific Opa1$^{-/-}$ Mice Treated with Combination of Metformin and Galantamine Maintained Fat Mass, Restored Metabolism and Prevented Liver Steatosis Treatment with combination of metformin and galantamine had no effect on body weight (FIG. 8A) and lean mass (FIG. 8B) in female Opa1$^{-/-}$ mice. However, fat mass was maintained in treated female Opa1$^{-/-}$ mice with advancing age (FIG. 8C), which has been associated with increased survival in rodent and human studies[20,21,22]. In parallel, the male treated Opa1$^{-/-}$ mice partially prevented white adipose tissue loss (FIG. 8D). Although the female treated Opa1$^{-/-}$ mice had an increased fat mass compared to the untreated Opa1$^{-/-}$ mice, this group consumed the same amount of calories (FIG. 8E). Next, the relationship between body mass and metabolic rate was explored by evaluating in vivo metabolism using the PhenoMaster metabolic cages system. Indirect calorimetry revealed that the combination of galantamine and metformin normalized both oxygen consumption and carbon dioxide production, especially during the light phase, in female Opa1$^{-/-}$ mice to control mice (FIG. 8F and FIG. 8G). In parallel, treated female Opa1$^{-/-}$ mice had increased energy expenditure compared to untreated Opa1$^{-/-}$ mice, despite and increased fat mass (FIG. 8H). Therefore, the increased fat mass observed in the treated Opa1$^{-/-}$ mice cannot be explained by food intake or energy expenditure. These data suggest that the combination treatment with galantamine and metformin corrects for the extremely fasted phenotype observed in untreated Opa1$^{-/-}$ mice. Next, to asses liver steatosis in these mice we performed an Oil red O staining. Untreated female Opa1$^{-/-}$ mice displayed liver steatosis which was completely prevented in the treated Opa1$^{-/-}$ mice. Muscle expression levels of IL6 in female Opa1$^{-/-}$ treated mice were normalized to control levels, indicative of decreased inflammation (FIG. 8I).

Combination of Metformin and Galantamine Improved Physical Performance in Muscle Specific Opa1$^{-/-}$ Mice.

Figure 9A:
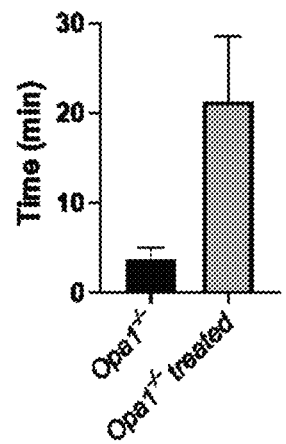
FIG. 9A-FIG. 9F. Combination of both metformin and galantamine improved physical performance in muscle specific Opa1$^{-/-}$ mice.
Figure 9B:
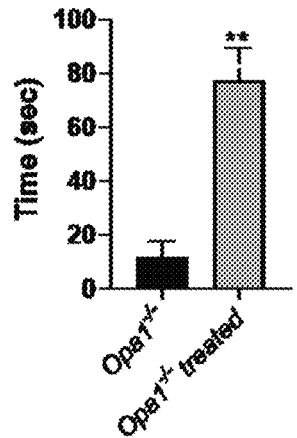
Figure 9C:
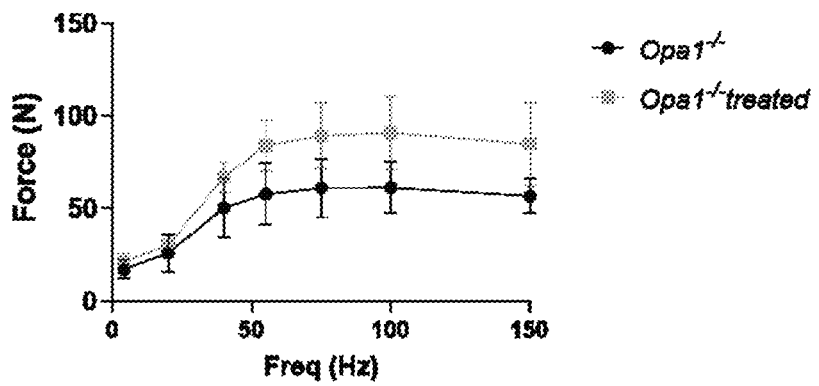
Figure 9D:
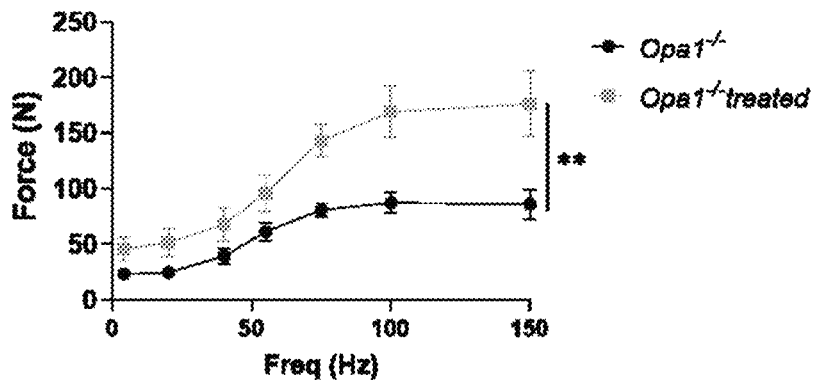
Figure 9E:
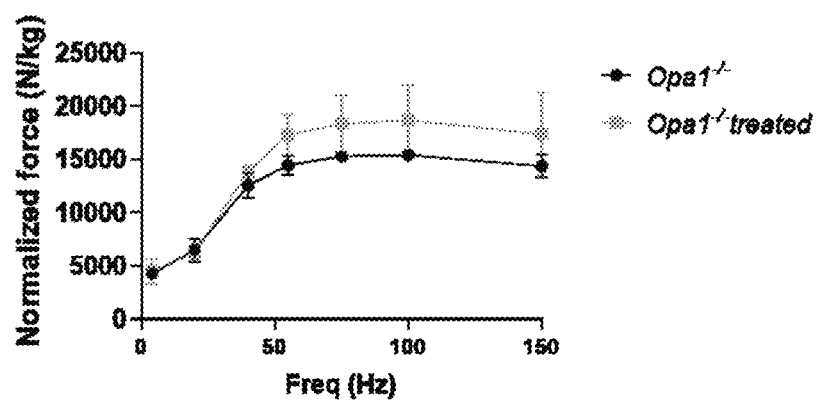
Figure 9F:
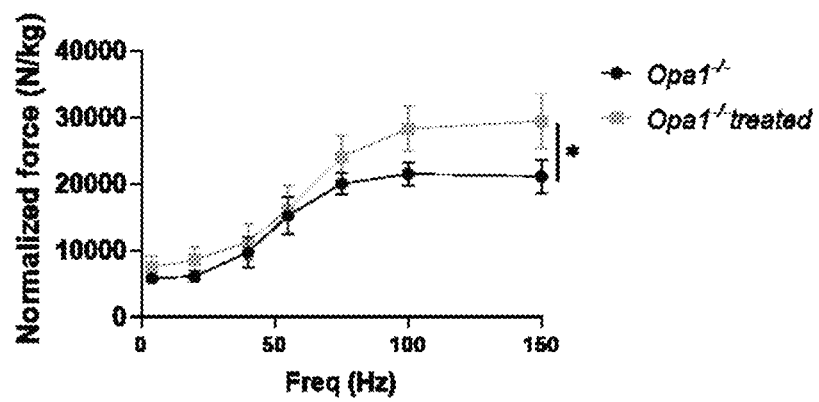

Next, we determined whether physical performance, an important health span marker, was preserved in treated Opa1$^{-/-}$ mice. To ascertain physical health of these animals, we included treadmill, grip strength and force measurements. Treated female Opa1$^{-/-}$ mice ran three times as long as the untreated Opa1$^{-/-}$ mice (FIG. 9A). Further, a significant effect with the combination treatment was observed with grip strength (FIG. 9B). The treatment showed an increase on absolute force (FIG. 9C) and on maximal specific force (FIG. 9E), generated during tetanic contraction, in treated female Opa1$^{-/-}$ mice, but this effect was not significant. The lack of significance in the females is probably a result of insufficient number and the greater biological variability. However, in male Opa1$^{-/-}$ treated mice a significant increase on absolute force (FIG. 9D) and maximal specific force (FIG. 9E and FIG. 9F) was observed compared to untreated Opa1$^{-/-}$ mice, indicating reduced muscle weakness in the treated Opa1$^{-/-}$ mice. Overall, these tests indicate that the combination of galantamine and metformin improved the general fitness of the Opa1$^{-/-}$ mice, which is associated with lower all-cause and cardiovascular mortality rates[23].

Combination of Metformin and Galantamine Partly Preserved Muscle Mass in Opa1$^{-/-}$ Mice Muscles of both the untreated and treated Opa1$^{-/-}$ mice are smaller compared to control mice, both in females (FIGS. 10A-FIG. 10C) as males (FIGS. 10D-FIG. 10F). In females, the tibialis anterior muscle, a glycolytic type II (fast-twitch) fiber, was partly preserved in the treated Opa1$^{-/-}$ mice (FIG. 10A), whereas in males the gastrocnemius and soleus muscle was partly rescued in treated Opa1$^{-/-}$ mice (FIG. 10E). This is an important finding as the age-associated muscle atrophy is higher in the glycolytic muscles (tibialis anterior, gastrocnemius) compared to oxidative muscles (e.g. soleus muscle). Succinate dehydrogenase (SDH) staining was increased in female Opa1$^{-/-}$ untreated mice compared control and Opa1$^{-/-}$ untreated animals, indicative of increased oxidative metabolism. However, regions of myofiber type IIA cytoplasm are devoid of mitochondria in the untreated Opa1$^{-/-}$ mice (histopathology data on file), a pattern of localization that resembles central core disease, and this was maintained in the treated Opa1$^{-/-}$ mice. In line with the SDH staining, increased type IIA fibers were observed in the untreated Opa1$^{-/-}$ animals compared to control and treated Opa1$^{-/-}$ mice (FIG. 10G). Next, we examined the expression of the neural cell adhesion molecule (NCAM), a molecule that is enriched in the postsynaptic membrane of the neuromuscular junction (NMJ) but largely absent in adult myofibers. However, after the loss of innervation, NCAM is re-expressed along the entire muscle fiber. Importantly, loss of myofiber innervation, that occurs during normal aging and which coincides with an acceleration of muscle atrophy, was partly prevented in treated female Opa1$^{-/-}$ mice as shown by reduced NCAM positive fibers (FIG. 10H). Moreover, bone health will also be assessed in these mice. Several parameters (e.g. trabecular bone volume, trabecular connectivity and trabecular bone mineral density and cortical thickness) will be evaluated with micro-CT. Opa1$^{-/-}$ mice will further be treated with the individual components galantamine and metformin individually and the same analysis as described above will be performed.

Combination of Metformin and Galantamine on Physiological, Metabolic and Functional Health Trajectories Longitudinally The effect of the combination drug (metformin plus galantamine) on physiological, metabolic, and functional health trajectories will be measured in two strains of mice and both sexes throughout their lifespan, called study of longitudinal aging in mice-2 (SLAM-2). The set-up of this study is based on the SLAM-1 study at the National Institute on Aging (NIH, USA), that tested for the same aging and age-related phenotypes but without an intervention. SLAM-2 will be a very extensive study, starting measurements in mice at an age of 12 months. At different endpoints throughout life various tests will be performed with the focus mainly on four key aging phenotypes: metabolic (e.g. diabetes, NAFLD, metabolic syndrome), neuromuscular (e.g. sarcopenia, osteoporosis, NMJ stability), cardiovascular (e.g. heart failure) and cognition (e.g. Alzheimer), which have high relevance to human health as these domains are the leading cause of disability, mortality and morbidity. Results of SLAM-2 will reveal how trajectories of biological and physiological parameters change with the intervention of a compound known to have positive effects on healthy aging, compared to baseline results of SLAM-1.

Moreover, in a separate study, the efficacy on health span and life span of both the individual compounds as well as the combination drug will be examined. A battery of tests similar to those described in SLAM-2 will be performed longitudinally at regular intervals, weekly and monthly, across the lifespan of the animals.

Combination of Metformin and Galantamine on Promoting Improved Resiliency

In parallel with the unstressed studies, the effects of the combination of metformin and galantamine will be examined in the context of stressed (resiliency) models. Three of the more common clinical ailments associated with human aging are obesity-related type II diabetes (induced by overnutrition), sarcopenia (long-term bedrest) and neuromuscular junction instability (trauma, surgery). Three well-established and time-efficient mouse models that can be used to examine these complications+/−combination of both metformin and galantamine are (I) high-fat diet (HFD) fed mice, (II) hindlimb suspension, and (III) sciatic nerve crush or cut, respectively. In the context of these models, a panel of standardized short-term tests will be performed in young and middle-aged mice to determine the effectiveness of the combination of metformin and galantamine on promoting improved resiliency.

Example 3: Human Study

A. Proof-of-Concept Study in Patients with Sarcopenic Obesity

This exploratory proof-of-concept study will be performed to assess to what extent the combination of metformin and galantamine has a favorable impact on sarcopenic parameters of muscle mass and muscle strength in patients with sarcopenic obesity. It also intends to assess the effect of different dosages of metformin and galantamine on the parameters to be assessed, including biomarkers of aging. This study is a randomized, double-blind, placebo-controlled proof-of-concept study of 24 weeks, consisting of 3 consecutive 8-week treatment periods with 3 increasing dose levels.

Metformin will be provided as immediate release, sustained release, delayed release or controlled release formulation, allowing daily dosages to be provided of 250 mg (dose level 1), 500 mg (dose level 2) and 1000 mg (dose level 3). Galantamine will be provided as immediate release or sustained release formulation, allowing daily dosages to be provided of 3 mg (dose level 1), 6 mg (dose level 2) and 12 mg (dose level 3). The combination of metformin and galantamine will be provided as a fixed combination, for example of 250 mg metformin and 3 mg galantamine (dose level 1), 500 mg metformin and 6 mg galantamine (dose level 2) and 1000 mg metformin and 12 mg galantamine (dose level 3). Matching formulations of placebo will be provided.

B. Proof-of-Concept Study in Sarcopenic Patients Undergoing Total Hip Arthroplasty This exploratory proof-of-concept study is designed to assess to what extent the combination of metformin and galantamine has a favorable impact on sarcopenic parameters of muscle mass and muscle strength in patients with sarcopenia who are scheduled for total hip arthroplasty (THA) of the hip. It is also designed to assess if and to what extent patients treated with the combination of metformin and galantamine experience a better functional outcome after THA. This study is a randomized, double-blind, placebo-controlled exploratory proof-of-concept study of 24 weeks, consisting of a 12-week treatment phase prior to surgery and a 12-week treatment phase after surgery.

The combination of metformin and galantamine will be provided as a fixed combination of for example 250 mg metformin and 3 mg galantamine (dose level 1), 500 mg metformin and 6 mg galantamine (dose level 2) and 1000 mg metformin and 12 mg galantamine (dose level 3). Matching formulations of placebo will be provided. The treatment is partially before surgery and partially post-operative.

REFERENCES

1. De Haes, W. et al. Metformin promotes lifespan through mitohormesis via the peroxiredoxin PRDX-2. *Proc. Natl. Acad. Sci.* 111, E2501-E2509 (2014).
2. Wilkinson, D. S., Taylor, R. C. & Dillin, A. Analysis of aging in *Caenorhabditis elegans*. *Methods Cell Biol.* 107, 353-381 (2012).
3. Churgin, M. A. et al. Longitudinal imaging of *Caenorhabditis elegans* in a microfabricated device reveals variation in behavioral decline during aging. *Elife* 6, (2017).
4. Lucanic, M. et al. Standardized Protocols from the *Caenorhabditis* Intervention Testing Program 2013-2016: Conditions and Assays used for Quantifying the Development, Fertility and Lifespan of Hermaphroditic *Caenorhabditis* Strains. *Protoc. Exch.* (2017).
5. Keith, S. A., Amrit, F. R. G., Ratnappan, R. & Ghazi, A. The *C. elegans* healthspan and stress-resistance assay toolkit. *Methods* 68, 476-486 (2014).
6. Hahm, J.-H. et al. *C. elegans* maximum velocity correlates with healthspan and is maintained in worms with an insulin receptor mutation. *Nat. Commun.* 6, 8919 (2015).

7. Hsu, A.-L., Feng, Z., Hsieh, M.-Y. & Xu, X. Z. S. Identification by machine vision of the rate of motor activity decline as a lifespan predictor in *C. elegans*. *Neurobiol. Aging* 30, 1498-1503 (2009).
8. Peymen, K. et al. Myoinhibitory peptide signaling modulates aversive gustatory learning in *Caenorhabditis elegans*. *PLOS Genet.* 15, e1007945 (2019).
9. Dues, D. J. et al. Aging causes decreased resistance to multiple stresses and a failure to activate specific stress response pathways. *Aging* (Albany. NY). 8, 777-795 (2016).
10. McElwee, J. J. et al. Evolutionary conservation of regulated longevity assurance mechanisms. *Genome Biol.* 8, R132 (2007).
11. Detienne, G., Van de Walle, P., De Haes, W., Schoofs, L. & Temmerman, L. SKN-1-independent transcriptional activation of glutathione S-transferase 4 (GST-4) by EGF signaling. *Worm* 5, e1230585 (2016).
12. Herndon, L. A. et al. Stochastic and genetic factors influence tissue-specific decline in ageing *C. elegans*. *Nature* (2002).
13. Borisy, A. A. et al. Systematic discovery of multicomponent therapeutics. *Proc. Natl. Acad. Sci.* 100, 7977-7982 (2003).
14. Cabreiro, F. et al. Metformin Retards Aging in *C. elegans* by Altering Microbial Folate and Methionine Metabolism. *Cell* 153, 228-239 (2013).
15. Benedetto, A. et al. LFASS: Label-free automated survival scoring for high-throughput nematode assays. *Aging Cell* in press (2019).
16. Tezze, C. et al. Age-Associated Loss of OPA1 in Muscle Impacts Muscle Mass, Metabolic Homeostasis, Systemic Inflammation, and Epithelial Senescence. *Cell Metab.* 25, 1374-1389.e6 (2017).
17. Cogliati, S. et al. Mitochondrial cristae shape determines respiratory chain supercomplexes assembly and respiratory efficiency. *Cell* 155, 160-171 (2013).
18. Weir, J. B. de V. New methods for calculating metabolic rate with special reference to protein metabolism. *J. Physiol.* 109, 1-9 (1949).
19. Blaauw, B. et al. Akt activation prevents the force drop induced by eccentric contractions in dystrophin-deficient skeletal muscle. *Hum. Mol. Genet.* 17, 3686-3696 (2008).
20. Mitchell, S. J. et al. Effects of Sex, Strain, and Energy Intake on Hallmarks of Aging in Mice. *Cell Metab.* 23, 1093-1112 (2016).
21. Liao, C. Y. et al. Fat maintenance is a predictor of the murine lifespan response to dietary restriction. *Aging Cell* 10, 629-639 (2011).
22. Flegal K M, Kit B K, Orpana H, G. B. Association of all-cause mortality with overweight and obesity using standard body mass index categories. *J. Am. Med. Assoc.* 97, 3855-63 (2013).
23. Kokkinos, P. Physical Activity, Health Benefits, and Mortality Risk. *ISRN Cardiol.* 2012, 1-14 (2012).

The invention claimed is:

1. A method for treating or stabilizing a neuromusculoskeletal disease, the method comprising:
administering to a subject in need thereof a pharmaceutical combination comprising:
metformin, or an N-oxide, a hydrate, a pharmaceutically acceptable salt or solvate thereof; and
an acetylcholinesterase inhibitor, or an N-oxide, a hydrate, a pharmaceutically acceptable salt or solvate thereof, wherein the acetylcholinesterase inhibitor is selected from the group consisting of galantamine, donepezil, rivastigmine, and memantine.

2. The method of claim 1, wherein the acetylcholinesterase inhibitor is galantamine.

3. The method of claim 1, wherein the metformin and the acetylcholinesterase inhibitor are each administered in a subtherapeutic dose to the subject.

4. The method of claim 1, wherein the subject is a human subject.

5. A method for improving a measure of life span and/or health span in a subject suffering from a neuromusculoskeletal disease, the method comprising:
administering to the subject a pharmaceutical combination comprising:
metformin, or an N-oxide, a hydrate, a pharmaceutically acceptable salt or solvate thereof; and
an acetylcholinesterase inhibitor, or an N-oxide, a hydrate, a pharmaceutically acceptable salt or solvate thereof, wherein the acetylcholinesterase inhibitor is selected from the group consisting of galantamine, donepezil, rivastigmine, and memantine;
wherein:
the improved measure of life span and/or health span is the lessening or reduction in the severity of at least one clinical symptom associated with the neuromusculoskeletal disease.

6. The method of claim 1, wherein treating or stabilizing the neuromusculoskeletal disease comprises lessening or reducing the severity of at least one clinical symptom associated with the neuromusculoskeletal disease.

7. The method of claim 1, wherein the metformin is administered in a dose of from about 5 mg/day to about 1500 mg/day and the acetylcholinesterase inhibitor is administered in a dose of less than about 16 mg/day.

8. The method of claim 1, wherein the metformin is administered in a dose of from about 5 mg/day to about 1000 mg/day and the acetylcholinesterase inhibitor is administered in a dose of less than about 16 mg/day.

9. The method of claim 1, wherein the neuromusculoskeletal disease is selected from extrapyramidal disorders, diseases of the myoneural junction, systemic atrophies primarily affecting the central nervous system, muscular dystrophy, duchenne muscular dystrophy, spinal muscular atrophy, ataxia, or sarcopenia.

10. The method of claim 1, wherein the neuromusculoskeletal disease is sarcopenia.

* * * * *

UNITED STATES PATENT AND TRADEMARK OFFICE
CERTIFICATE OF CORRECTION

PATENT NO. : 12,090,124 B2
APPLICATION NO. : 17/255662
DATED : September 17, 2024
INVENTOR(S) : Ann Beliën Page 1 of 1

It is certified that error appears in the above-identified patent and that said Letters Patent is hereby corrected as shown below:

In the Specification

In Column 10, Line(s) 47, after "system", insert --.--.

In Column 26, Line(s) 53, delete "100 UM" and insert --100 µM--, therefor.

Figure 4A:
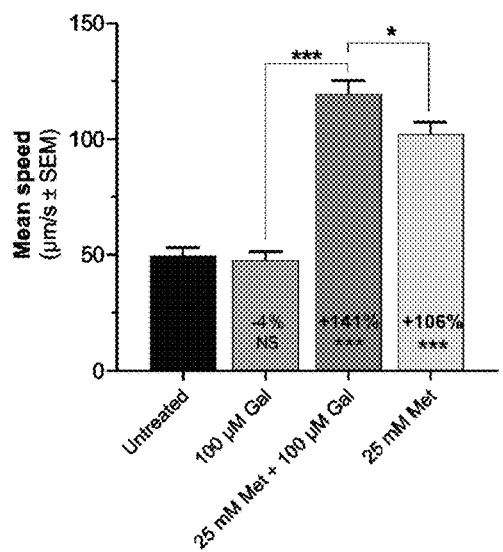
FIG. 4A-FIG. 4D. Repeated dosing of *C. elegans* with galantamine and/or metformin positively impacts multiple locomotion and behavioral parameters in post-reproductive adults (Mean speed (FIG. 4A), Max speed (FIG. 4B), Fraction running (FIG. 4C), Cell occupancy (FIG. 4D)). Error bars indicate SEM. Statistical significance levels (and percentual changes) are indicated versus the untreated control at the bottom of each chart. Statistical significance versus '25 mM Met+100 UM Gal' is indicated via additional lines. $*p<0.05$, $p<0.01$, $*p<0.001$, NS not significant. Full locomotion data are displayed in Table 2.
Figure 4B:
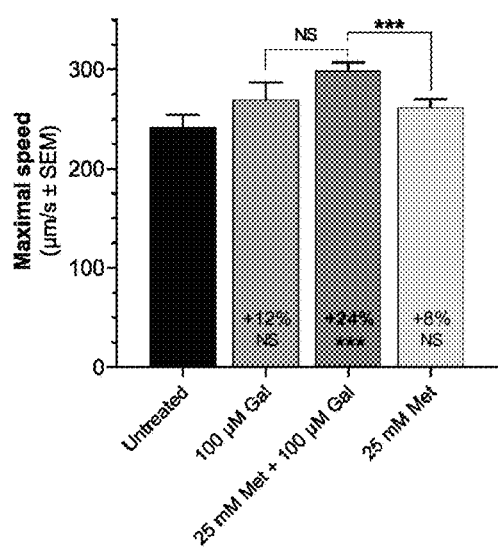
Figure 4C:
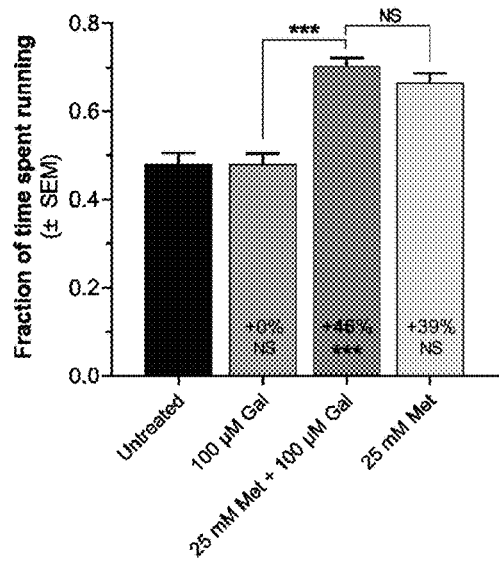
Figure 4D:
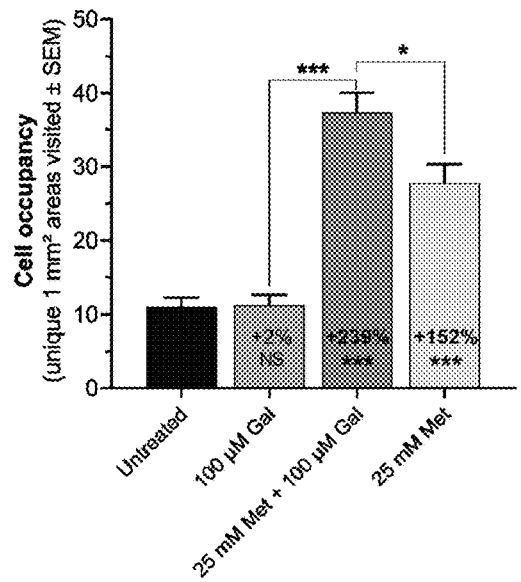

In Column 27, table 2, delete "Data corresponds to FIG. 4." and insert --Data corresponds to FIG. 4A - FIG. 4D, with FIG. 4A) depicting mean speed, FIG. 4B) maximal speed, FIG. 4C) fraction of time spent running, and FIG. 4D) cell occupancy.--, therefor.

Figure 5A:
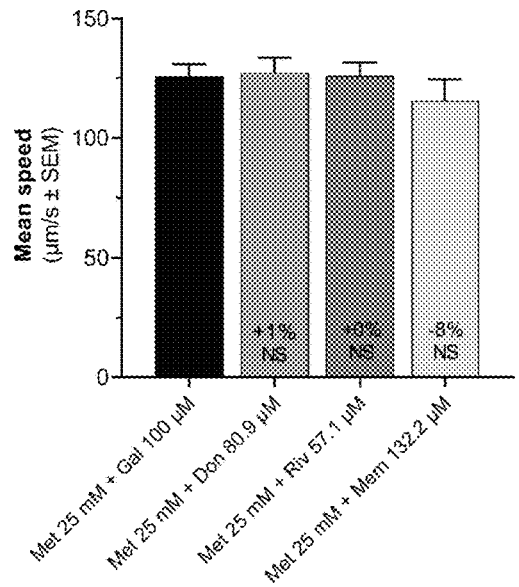
FIG. 5-FIG. 5D. The combination of 25 mM Met with the acetylcholinesterase inhibitors Don and Riv or the acetylcholinesterase inhibitor-like compound Mem induces very a similar locomotion phenotype as the combination of 25 mM Met with the acetylcholinesterase inhibitor Gal (Mean speed (FIG. 5A), Max speed (FIG. 5B), Fraction running (FIG. 5C), Cell occupancy (FIG. 5D)). Statistical significance levels (and percentual changes) are indicated versus the untreated control at the bottom of each chart. $*p<0.05$, NS not significant. Full locomotion data are displayed in Table 3.
Figure 5B:
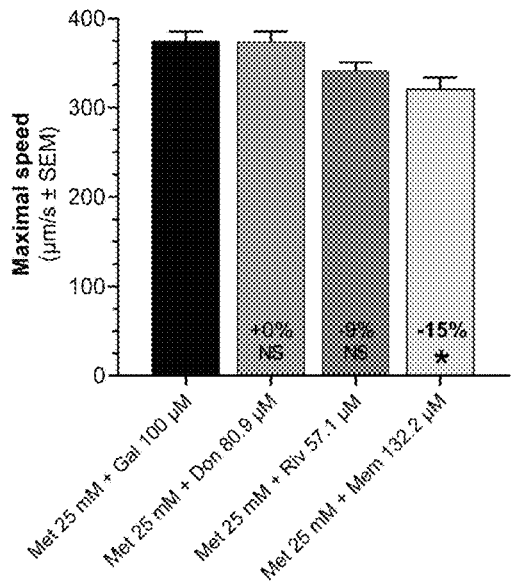
Figure 5C:
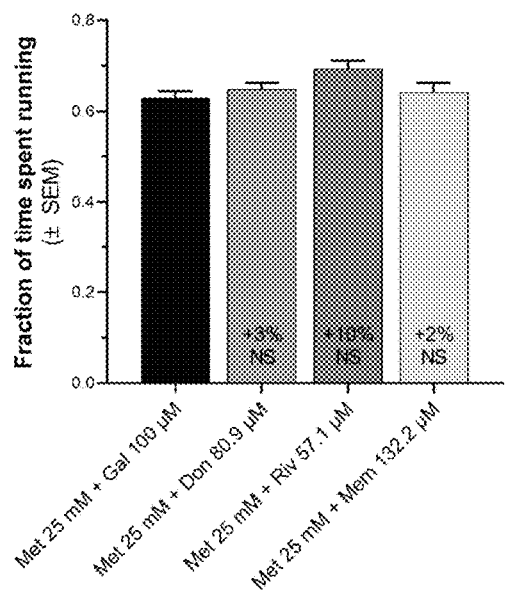
Figure 5D:
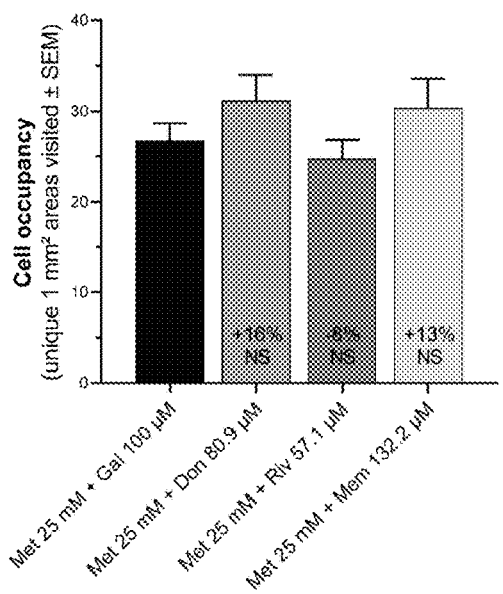

In Column 27, table 3, delete "Data corresponds to FIG. 5." and insert --Data corresponds to FIG. 5A - FIG. 5D, with FIG. 5A) depicting mean speed, FIG. 5B) maximal speed, FIG. 5C) fraction of time spent running, and FIG. 5D) cell occupancy.--, therefor.

Signed and Sealed this
Second Day of September, 2025

Coke Morgan Stewart
*Acting Director of the United States Patent and Trademark Office*